US008722076B2

(12) United States Patent
Rolfes Meyering et al.

(10) Patent No.: US 8,722,076 B2
(45) Date of Patent: May 13, 2014

(54) PHOTOCHROME- OR NEAR IR DYE-COUPLED POLYMERIC MATRICES FOR MEDICAL ARTICLES

(75) Inventors: Emily R. Rolfes Meyering, Eden Prairie, MN (US); Aron B. Anderson, Minnetonka, MN (US)

(73) Assignee: SurModics, Inc., Eden Prairie, MN (US)

( * ) Notice: Subject to any disclaimer, the term of this patent is extended or adjusted under 35 U.S.C. 154(b) by 40 days.

(21) Appl. No.: 13/248,203

(22) Filed: Sep. 29, 2011

(65) Prior Publication Data

US 2012/0082713 A1 Apr. 5, 2012

Related U.S. Application Data

(60) Provisional application No. 61/388,274, filed on Sep. 30, 2010, provisional application No. 61/447,029, filed on Feb. 26, 2011.

(51) Int. Cl.
| A61F 2/00 | (2006.01) |
| A61K 9/00 | (2006.01) |
| A61F 13/00 | (2006.01) |
| C08F 26/06 | (2006.01) |

(52) U.S. Cl.
USPC ............ 424/423; 424/400; 424/422; 526/258

(58) Field of Classification Search
None
See application file for complete search history.

(56) References Cited

U.S. PATENT DOCUMENTS

| 3,597,446 | A |  | 8/1971 | Poot |
| 3,671,543 | A |  | 6/1972 | Koga et al. |
| 3,896,126 | A |  | 7/1975 | Oberlinner et al. |
| 3,997,627 | A |  | 12/1976 | Ichimura et al. |
| 4,287,337 | A |  | 9/1981 | Guglielmetti et al. |
| 4,851,530 | A |  | 7/1989 | Rickwood |
| 4,980,089 | A |  | 12/1990 | Heller |
| 5,002,582 | A |  | 3/1991 | Guire et al. |
| 5,241,075 | A |  | 8/1993 | Hibino et al. |
| 5,414,075 | A |  | 5/1995 | Swan et al. |
| 5,563,056 | A |  | 10/1996 | Swan et al. |
| 5,637,460 | A |  | 6/1997 | Swan et al. |
| 5,708,181 | A |  | 1/1998 | Hama et al. |
| 5,714,360 | A |  | 2/1998 | Swan et al. |
| 5,807,605 | A |  | 9/1998 | Tingey et al. |
| 5,821,287 | A | * | 10/1998 | Hu et al. .................... 524/89 |
| 5,858,653 | A |  | 1/1999 | Duran et al. |
| 6,156,345 | A |  | 12/2000 | Chudzik et al. |
| 6,211,374 | B1 | * | 4/2001 | Ippoliti ................... 546/153 |
| 6,278,018 | B1 |  | 8/2001 | Swan |
| 6,362,248 | B1 |  | 3/2002 | Hara et al. |
| 6,410,044 | B1 |  | 6/2002 | Chudzik et al. |
| 7,052,512 | B2 |  | 5/2006 | Yang et al. |
| 7,056,533 | B2 | * | 6/2006 | Chudzik et al. ............ 424/486 |
| 7,429,623 | B2 |  | 9/2008 | Molock et al. |
| 7,592,418 | B2 |  | 9/2009 | Pathak et al. |
| 2003/0017073 | A1 | * | 1/2003 | Eckhardt et al. ............ 422/24 |
| 2005/0254003 | A1 | * | 11/2005 | Jani et al. ................... 351/160 R |
| 2006/0287410 | A1 |  | 12/2006 | Chudzik et al. |
| 2007/0197750 | A1 |  | 8/2007 | Gibanel et al. |
| 2008/0261323 | A1 | * | 10/2008 | Diamond et al. ............ 436/166 |
| 2011/0144373 | A1 |  | 6/2011 | Swan et al. |
| 2011/0245367 | A1 |  | 10/2011 | Kurdyumov et al. |

FOREIGN PATENT DOCUMENTS

| WO | WO 97/22037 | 6/1997 |
| WO | WO 01/02449 | 1/2001 |
| WO | WO 01/90268 | 11/2001 |
| WO | WO 03/022322 | 3/2003 |
| WO | WO 2004/056406 | 7/2004 |
| WO | WO 2006/119328 | 11/2006 |
| WO | WO 2007/027479 | 3/2007 |
| WO | WO 2010/039653 | 4/2010 |

OTHER PUBLICATIONS

Wikipedia, Pegylation, (Dec. 17, 2008), pp. 1-4.*
Amiot, C.L., et al., (2008) *Near-Infrared Fluorescent Materials for Sensing of Biological Targets*, Sensors 8: 3082-3105.
Cipolloni, M., et. al., (2008) *New Thermally Irreversible and Fluorescent Photochromic Diarylethenes*, J. Phys. Chem. A 112: 4765-4771.
Cusido, J., et al., (2009) *Fluorescent Switches Based on Photochromic Compounds*, Eur J. Org. Chem. 2031-2045.
Delbaere, S., et al., (2006) *Controlled Conversion of Isomers in a Hybrid Biphotochromic System*, Org. Lett., 8: 4931-4934.
di Nunzio, M.R., et al., (2008) *Photochromic, Thermochromic, and Fluorescent Spirooxazines and Napthopyrans: A Spectrokinetic and Thermodynamic Study*, ChemPhysChem 9: 768-775.
Fischer, G.M., et al., (2009) *Pyrrolopyrrole Cyanine Dyes: A New Class of Near-Infrared Dyes and Fluorophores*, Chem. Eur. J. 15: 4857-4864.
Jyothish, K., et al., (2007) *Development of squaraine dyes for photodynamic therapeutical applications: synthesis and study of electronic factors in the dye formation reaction*, ARKIVOC (viii): 296-310.
Meek, S.T., et al., (2008) *Near-Infrared Fluorophores Containing Benzo[c]heterocycle Subunits*, Org. Lett., 10: 2991-2993.

(Continued)

*Primary Examiner* — Scott Long
*Assistant Examiner* — Lyndsey Beckhardt
(74) *Attorney, Agent, or Firm* — Kagan Binder, PLLC

(57) ABSTRACT

The invention provides polymers comprising pendent photochrome or near IR dye groups, as well as polymeric matrices made from these polymers, which can be used as or in association with a medical article. The polymers can be synthesized using methods that facilitate the preparation of medical articles having good biocompatibility. Exemplary polymeric matrices are in the form of lubricious coatings on medical devices, such as catheters. Visualization by irradiation of the photochrome or near IR dye can improve detection of the polymeric matrix on a device or in the body. This, in turn can improve aspects of a medical procedure, such as device insertion or matrix formation, as well as being useful for assessing the quality of the matrix.

9 Claims, No Drawings

(56) References Cited

OTHER PUBLICATIONS

Raymo, F.M., et al., (2005) *Fluorescence Modulation with Photochromic Switches*, J. Phys. Chem. A 109: 7343-7352.

Samanta, A., et al., (2010) *Development of photostable near-infrared cyanine dyes*, Chem. Commun., 46: 7406-7408.

Tatarets, A.L., et al., (2006) *Synthesis of water-soluble, ring-substituted squaraine dyes and their evaluation as fluorescent probes and labels*, Analytica Chimica Acta 570: 214-223.

Tomasulo, M., et al., (2008) *Bichromophoric Photochromes Based on the Opening and Closing of a Single Oxazine Ring*, J. Org. Chem, 73: 118-126.

Traven, V.F., et al., (2008) *Coumarinyl(thienyl)thiazoles: Novel Photochromes with Modulated Fluorescence*, Organic Letters 10: 1319-1322.

Yagi, K., et al., (2001) *Syntheis of Fluorescent Diarylethenes Having a 2, 4, 5- Triphenylimidazole Chromophore*, J. Org. Chem. 66: 5419-5423.

\* cited by examiner

PHOTOCHROME- OR NEAR IR DYE-COUPLED POLYMERIC MATRICES FOR MEDICAL ARTICLES

PRIORITY CLAIM

This application claims the benefit of U.S. Provisional Patent Application Ser. No. 61/388,274 filed Sep. 30, 2010, entitled PHOTOCHROME-COUPLED POLYMERIC MATRICES FOR MEDICAL ARTICLES, and U.S. Provisional Patent Application Ser. No. 61/447,029 filed Feb. 26, 2011, entitled PHOTOCHROME- OR NEAR IR DYE-COUPLED POLYMERIC MATRICES FOR MEDICAL ARTICLES, the disclosures of which are incorporated herein by reference.

FIELD OF THE INVENTION

The invention relates to biocompatible photochrome- or near IR dye-coupled polymers and polymeric matrices made therefrom for medical use.

BACKGROUND OF THE INVENTION

Biocompatible polymers have been used to prepare biodegradable polymeric matrices that can be associated with, or formed into, implantable medical devices. For example, biocompatible polymers can be used to make a coating on the medical device's surface, or an in-situ formed hydrogel which can be used for tissue treatment or a sealant. If the biocompatible polymer has thermoplastic properties, it can even be molded or formed into a shape to provide an implantable device having a structural property useful for treating a medical condition at the site of implantation.

For example, polymeric surface coatings can provide medical articles, such as those that are implanted or temporarily inserted into the body, with a variety of distinct benefits. These benefits include lubricity and wettability, passivity against protein absorption, antimicrobial properties, drug delivery, biocompatibility, and hemocompatibility. The demand for medical articles having these types of coatings has been appreciated because they generally improve the function of the device upon implantation or insertion in the body. For example, a lubricious polymeric coating may have properties which reduce frictional forces when the device is introduced and moved within the body. Various catheter types are examples of medical articles that may be provided with hydrophilic coatings. Hydrophilic coatings are generally known in the art of implantable medical devices.

Detection of portions of an implantable medical device can be useful after implantation of a device, as well as prior to implantation. Reagents such as paramagnetic materials and radioisotopes can allow detection of the device after it has been implanted, which can be very useful for tracking the movement and positioning of the device during an insertion process. Other reagents, such as colorants and dyes can also be used with a device to make it visually detectable. However, these reagents are not ideal for use in biocompatible polymeric matrices, especially those formed using irradiation.

The current invention relates to polymeric matrices made using a photochrome-coupled polymer, overcomes challenges in the art, and represents improvements with regards to properties such as biocompatibility and the maintenance of polymeric matrix properties.

SUMMARY OF THE INVENTION

Generally, the present invention is related to biocompatible polymers including a detection moiety that is coupled to the polymer, and polymeric matrices formed therefrom. The detection moiety can allow the polymeric matrix to be visualized when a source of energy is applied to the polymeric matrix. Exemplary detection moieties are those which emit or reflect light in the visible range, and therefore provide a way of determining the polymeric matrix when desired. Exemplary detection moieties are photochrome moieties and near infrared (IR) dyes.

In some aspects, the invention provides biocompatible photochrome-containing polymers or near IR dye-containing polymers, and polymeric matrices formed therefrom. The polymeric matrices can be formed into, or be used in conjunction with a medical article, such as a medical article that is inserted or implanted into a portion of the body, or formed at a target site in situ. The biocompatible photochrome- or near IR dye-containing polymers are synthesized to provide a polymer backbone with a covalently-bonded photochrome moiety or covalently-bonded near IR dye, respectively, pendent from the polymer backbone. The invention also provides synthesis methods for a photochrome- or near IR dye-containing polymer so a polymeric matrix formed from the polymer is biocompatible.

In some modes of practice, the polymeric matrix can be visualized by irradiating a polymer-bonded photochrome to cause a chemical transformation of the photochrome that changes its optical absorption and/or emission properties. For example, the photochrome can undergo a structural rearrangement to convert the molecule into an "open" form which is capable of absorbing wavelengths of light in the visible spectrum. As a result of the transformation of the photochrome, the polymeric matrix becomes detectable, such as by a color change detectable visually or using electronic equipment.

Photochromes that can transform into two independent light absorbers upon irradiation can be used in the polymer. For example, photoinduction of certain spirooxazine photochromes can promote the simultaneous formation of two chromophores able to absorb in the visible region. Photochrome "dyads," "hybrids," or "multi-photochromes" can also be used in the polymer. Exemplary multi-photochromes are compounds having two photochrome moieties, such as napthopyran-dithienylethene conjugates. Irradiation using different wavelengths of light can promote the formation of isomers which have various spectral characteristics.

A photochrome having a fluorescence property can be used in the polymer. Some fluorescent photochromes are absorptive to visible light and fluoresce under illumination. Certain photochromes can also fluoresce following UV illumination. Some fluorescent photochromes can change from fluorescent to non-fluorescent following illumination. Some fluorescent photochromes can be "hybrid" molecules that combine a fluorescent moiety and a non-fluorescent photochrome. The photochrome can have an emission spectrum that overlaps with the absorption spectrum of the fluorescence moiety when the photochrome moiety is in the transformed state. The polymeric matrix can be visualized by presence or absence of fluorescence of the fluorescence moiety, depending on the state of the photochrome. For example, the photochrome (when in a transformed state) transfers energy to the fluorescence moiety, and promotes visualization of the polymeric matrix by fluorescence. Use of such a biocompatible photochrome-containing polymer can provide the advantage of understanding whether the matrix has been irradiated, as well as visualization of the matrix.

Therefore, in some aspects, the invention includes the following photochrome-containing polymers: 1) a photochrome attached to the polymer, wherein the photochrome is absorptive to ultraviolet light and transforms to become absorptive to visible light (colored); 2) a photochrome attached to the polymer, wherein the photochrome transforms to become fluorescent under illumination; 3) a photochrome attached to the polymer, wherein the photochrome is absorptive to ultraviolet light and transforms to become both absorptive and fluorescent under visible light illumination; 4) a polymer that includes a photochrome and another fluorescent molecule, wherein the fluorescent molecule has an absorption spectrum that overlaps with the emission spectrum of the photochrome in the transformed state, wherein detection is based on fluorescence emission, which depends on the state of the photochrome; and 5) a photochrome type attached to the polymer, wherein the photochrome transforms upon ultraviolet illumination to two independent absorbers of light, such as one that is absorptive and optically detectable, and fluorescent.

In some cases, polymer-bonded near IR dyes are used to form the polymeric matrix. Near IR dyes generally absorb in the visible (400-700 nm) and/or near IR range (700-1000 nm) of the spectrum electromagnetic spectrum, and emit in the near IR range. Near IR emission from polymeric matrices can be detected using suitable detection equipment, such as digital camera sensors. Exemplary near IR dyes include benz (indolium) derivatives; cyanines including hydrocyanines, tricarboxycyanines, and indocyanines; squaraines and rotaxanes; and oxazins.

Visualization is useful for various processes associated with use of the medical article, including detection of the polymeric matrix during an insertion, implantation, or in situ formation process. Visualization can also be useful to assess the quality of the polymeric matrix. For example, in some aspects the invention provides a method for forming a polymeric matrix, such as a coating, which includes a step of irradiating the coating causing crosslinking and/or covalent immobilization of the polymeric material. In some modes of practice, irradiation of a photochrome-containing polymer during the crosslinking/immobilization process makes the polymeric material optically detectable, thereby allowing the user to confirm that the polymeric material was indeed irradiated. The use of a fluorescence photochrome provides increased sensitivity and allows for use of detection equipment that can quantitatively assess emission (fluorescence) from the irradiated polymer.

The invention provides biocompatible photochrome- or near IR dye-containing polymers having particular chemical features, and medical articles comprising polymeric matrices made using these polymers.

In one aspect, the biocompatible photochrome- or near IR dye-containing polymer includes a polymeric backbone and a pendent photochrome moiety or near IR dye moiety bonded to the polymer backbone in a particular chemical arrangement. In the arrangement, the photochrome moiety or near IR dye moiety includes a ring heteroatom, which is used to covalently bond the photochrome moiety or near IR dye moiety to the polymer backbone through a spacer group. The synthetic method used to form this photochrome-containing or near IR dye-containing polymer provides a biocompatible polymer preparation, and the preparation can be used to form all or a portion of a medical article, for example, a coating, an implantable medical device, or an in situ formed hydrogel. The biocompatibility of the preparation can advantageously carry over into the implantable medical device.

In a related aspect, the invention provides a method for making a biocompatible photochrome-containing polymer. The method includes the steps of (a) providing or obtaining a photochrome compound having a ring heteroatom; (b) reacting the photochrome compound with a spacer compound comprising a halide atom and a hydroxyl reactive group, the reaction involving nucleophilic substitution of the halide atom and covalent bonding to the heteroatom in the photochrome moiety to provide a photochrome-spacer compound, (c) reacting the photochrome-spacer compound with a free-radically polymerizable compound comprising a hydroxyl group to provide a photochrome-containing monomer; and (d) polymerizing the photochrome-containing monomer into a polymer.

In another aspect, the biocompatible photochrome-containing polymer includes a polymeric backbone, a pendent photochrome moiety or near IR dye bonded to the polymer backbone, and a pendent reactive group. The pendent reactive group allows for polymer crosslinking or bonding of the polymer to a target moiety, which can improve properties of the polymeric matrix, such as matrix durability and/or adhesion. In some aspects, the reactive group is a photoreactive group capable of activation and covalent bonding to a target moiety. The photoreactive group can be an aryl ketone species capable of UV light-induced activation. Other reactive groups which can be pendent from the photochrome-containing polymer include ethylenically unsaturated groups capable of being free-radically polymerized. In this sense, use of ethylenically unsaturated groups provides a photochrome- or near IR dye-containing macromer that can be used to enhance matrix formation.

In related aspects, the invention provides a method for forming a polymeric matrix. The method includes steps of providing a composition comprising a polymer comprising a photochrome-coupled or near IR dye-coupled monomeric unit and a pendent reactive group, and then treating the composition to activate the reactive group. Treatment can be by UV-irradiation in the case of a photoreactive pendent group, or polymerization initiation in the case of an ethylenically unsaturated group, to bond the polymer to a target moiety and/or cause polymer-polymer crosslinking.

Photochrome or near IR dyes having peak absorptions of about 650 nm or greater are preferred for use on polymer also having UV activated pendent reactive groups. Treatment of the polymer with UV irradiation to promote covalent crosslinking or bonding of the polymer to a surface to form the matrix results in minimal or no bleaching of the photochrome or near IR dye. The resulting polymeric matrix that is formed is able to subsequently irradiated at the absorption peak of the photochrome or near IR dye to allow for detection of the polymeric matrix.

Exemplary medical articles include those that are implantable, insertable, or formed in-situ. The matrix can form a portion of the medical article, such as a coating on a surface of an implantable or insertable medical device, for example, a coating on a guidewire or catheter. The coating can have lubricious properties, which can be provided by the photochrome- or near IR dye-containing polymer such as one formed predominantly from hydrophilic monomers. Optionally, the photochrome- or near IR dye-containing polymer can be blended with one or more hydrophilic polymers to provide a composition used to prepare a lubricious coating.

The polymeric matrix including the photochrome- or near IR dye-containing polymer can form a structural portion of the medical article, such as one that is an implant which provides a mechanical feature at the site of implantation. As another alternative, the polymeric matrix is in-situ formed, such as in the form of a hydrogel in contact with tissue. For example, the hydrogel can have function as a tissue sealant.

The invention also provides methods for the treatment of a subject using a medical article including a polymeric matrix comprising the photochrome- or near IR dye-containing polymer. Such treatment can involve the insertion, implantation, or formation of a medical article at a target location in the body. The medical article including a polymeric matrix comprising the photochrome- or near IR dye-containing polymer can be implanted or formed at a target location, or can be used to facilitate the implantation of a secondary medical device. Steps of treating the polymeric matrix (for example, by irradiation) and observing or analyzing its spectral properties are made possible by the light-induced change of the photochrome or IR emission from the near IR dye.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The present invention is directed to biocompatible photochrome- or near IR dye-containing polymers and medical articles formed from or associated with polymeric matrices made from compositions including these polymers.

As used herein a "polymeric matrix" refers to a mass of polymeric material that includes a biocompatible photochrome- or near IR dye-containing polymer of the invention. All or a portion of the polymeric matrix can be prepared from the biocompatible photochrome- or near IR dye-containing polymer. In some aspects, the polymeric matrix is predominantly or entirely formed from the biocompatible photochrome- or near IR dye-containing polymer. The polymeric matrix can be in various forms, such as in the form of a coating on a medical device, a filler material for a portion of a medical device, a three-dimensional implant, or an in situ-formed polymeric mass useful for a medical procedure.

The polymeric material in the matrix can be bonded together (for example, crosslinked), or not bonded together. The presence of such bonding may be dictated by the hydrophobe-hydrophile balance of the polymer, with more hydrophobic polymers tending to form polymeric matrices via hydrophobic interactions. In some cases the polymers of the matrix are associated via covalent bonding. Covalent bonding between polymeric material can be affected by various reactive chemistries, including free-radical polymerizable and photoreactive chemistries. Polymers having reactive pendent groups, or reactive crosslinking compounds, can be used to promote polymer crosslinking. In other aspects of the invention, the matrix is prepared using a photochrome- or near IR dye-containing polymer and a reactive chemistry that allows bonding of the photochrome- or near IR dye-containing polymer to a target moiety. The reactive chemistry can be a photoreactive group that upon exposure to UV irradiation is capable of being excited to an activated state, and then undergoes covalent bonding to a target moiety. Other reactive groups include free radically polymerizable groups, such as ethylenically unsaturated groups.

In some modes of practice, a biocompatible photochrome-containing polymer is synthesized by coupling a ring heteroatom in the photochrome moiety to a polymeric backbone group via a spacer group. The synthesis method can advantageously provide a biocompatible photochrome-containing polymer preparation, which otherwise avoids use of particular synthesis reagents, such as heavy metals, not desirably present in a composition that is used in the body.

The photochrome- and near IR dye-containing polymers and polymeric matrices including these polymers are "biocompatible," meaning that they do not produce an adverse biological affect that is detrimental to the medical condition of a subject, when the polymeric matrix is placed in the body at a target location. Biocompatible materials are generally not toxic or carcinogenic. However, it is understood that some therapeutic agents, which can optionally be associated with the polymeric matrix, function to treat a medical condition by killing or limiting the growth of certain cell or tissue types. Although these agents may have a negative effect on certain cells or tissues they can still be considered to be biocompatible because they are intended to treat a medical condition and improve the health of the treated subject in one or more ways.

The photochrome- or near IR dye-containing polymers may be described in terms of molecular weight. "Molecular weight," as used herein, more specifically refers to the "weight average molecular weight" or $M_w$, which is an absolute method of measuring molecular weight and is particularly useful for measuring the molecular weight of a polymer preparation. Polymer preparations typically include polymers that individually have minor variations in molecular weight. In some cases, the polymers have a relatively higher molecular weight (e.g., versus smaller organic compounds) and such minor variations within the polymer preparation do not affect the overall properties of the polymer preparation. The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

In many aspects, the polymeric matrix is in the form of a lubricious coating which is moved over tissue. In other aspects, the polymeric matrix is present at a target site in the body. The term "target site" refers to a location in or on a subject at which the polymeric matrix, alone or associated with a medical device, is formed or implanted. A site that is "in the body" is generally surrounded by body fluid or tissue. For example, a target site in the body can be a subdermal site, an intraperitoneal site, an intrathecal site, an intraocular site, an intravascular site, or an intramuscular site.

The term "in situ" (or "in vivo") is generally used to represent that the polymeric matrix is formed at a target location on the body or in the body. An in situ-formed polymeric mass can be one that sets up to a water-insoluble polymeric matrix when a composition containing the photochrome-containing polymer is delivered to a target site in or on the body.

A "treatment site" can include a target site as well as an area on or in the body that is to receive treatment directly or indirectly by the presence or use of the polymeric matrix.

Photochromes (also sometimes referred to as fluorochromes) are compounds capable of undergoing photochromism, which is the process of inducing a color change in a medium by incident electromagnetic radiation. Photochromes are capable of undergoing reversible changes in color. A photochrome can be irradiated to cause the opening of a ring structure in the photochrome moiety, which is referred to as the "transformed" configuration or state. The ring-opened photochrome absorbs light differently than the ring-closed from, and can be visualized by the induced color change. After a period of time the ring-opened form converts back to the ring closed form, and the induced color change is lost. In some cases the photochrome appears colored in the non-transformed state and color-less in the transformed state.

Some species of photochromes are absorptive to visible light and also fluoresce under visible light illumination. The photochrome can transform upon irradiation into two independent absorbers of light, which could provide optical (absorptive) visualization and fluorescence, detectably visibly or using electronic equipment.

In some aspects, the photochrome-containing polymer of the invention comprises a photochrome selected from the group consisting of spiropyrans, naphthopyrans, spiroxazines, spiroperimidines, diarylethenes, quinones, coumarins, and azobenzenes.

Photochromes that include a heteroatom in a ring structure of the core structure of the photochrome include spiropyrans, spiroxazines, and spiroperimidines.

Spiropyrans are based on the following core structure:

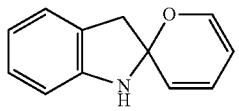 [SMILES: C1=COC2(C=C1)Cc1ccccc1N2]

An exemplary spiropyran (SP) has the following structure:

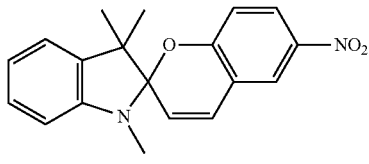

SP

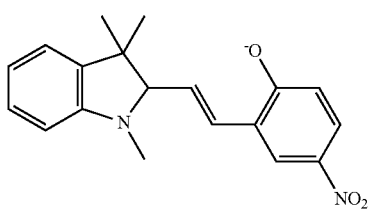

MC shown in the closed spiropyran (SP) form, and the open merocyanine (MC) form. Ultraviolet light converts the spiropyran to merocyanine. After irradiation with UV light, the ring-opened, and colored MC form slowly rearranges back to the SP form.

Another photochrome type is spirooxazine. Spirooxazines are based on the following core structure.

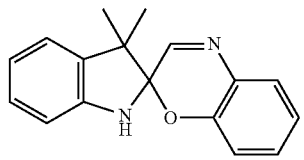 [SMILES: CC1(C)c2ccccc2NC12C=Nc1ccccc1O2]

Exemplary spirooxazines, including ones that fluoresce, are described by Nunzio et al. (Chem. Phys. Chem. 9, 768-775 (2008)). Nunzio's spirooxazines include 1,3-dihydro-3,3-dimethyl-1-isobutyl-6'-(2,3-dihydro-1H-indol-1-yl) spiro{2H-indole-2,3'-3H-naphtho[2,1-b][1,4]oxazine}(SO-1), and 1,3-dihydro-3,3-dimethyl-1-neopentyl-6'-(4''-N,N-diethylanilino)spiro {2H-indole-2,2'-3H-naphtho[1,2-b][1,4]oxazine} (SO-2) as shown below:

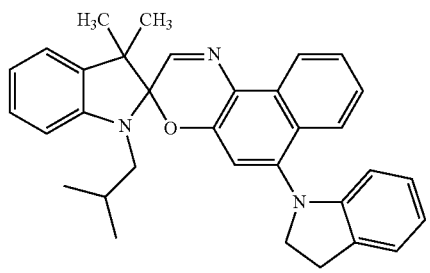

SO-1

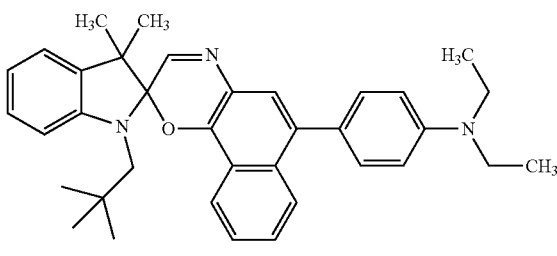

SO-2

SO-1 and SO-2 spirooxazines displayed fluorescence with wavelengths ($\lambda_{max}$) of 577 nm and 550 nm, respectively.

Other exemplary spirooxazines, including ones that are transformed into two independent light absorbers upon irradiation, are described by Tomasulo et al. (J. Org. Chem. 73, 118-126 (2008)). These bichromophoric photochromes were prepared by incorporating fused 3H-indole and 4-nitrophenoxy fragments and pendant biphenyl, styryl, biphenylvinyl, or stilbenzylvinyl groups. Laser excitation cleaves a [C—O] bond and opens the [1,3]oxazine ring, generating simultaneously a 4-nitrophenolate anion and a 3H-indolium cation. Photoinduction of these spirooxazines promotes the simultaneous formation of two chromophores able to absorb in the visible region in a single photochemical event.

Another photochrome type is spiroperimidine. An exemplary spiroperimidine has the following structure:

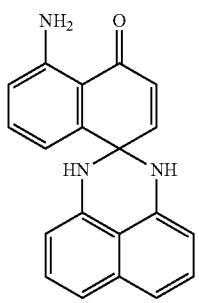 [SMILES: Nc1cccc2c1C(=O)C=CC21Nc2cccc3cccc(c23)N1]

and chemical name of 2,3-dihydro-2-spiro-4'-[8'-aminon-apthalen-1'(4'H)-one]perimidine. Another exemplary spiroperimidine has the following structure:

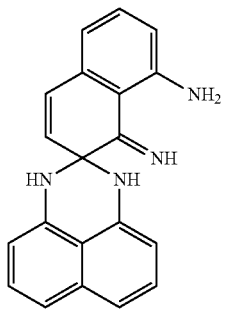 [SMILES: N=C1c2c(N)cccc2C=CC12Nc1cccc3cccc(c13)N2]

and chemical name of 2,3-dihydro-2-spiro-7'-[8'-imino-7',8'-dihydronapthalen-1'-amine]perimidine.

Another photochrome type is naphthopyran. Naphthopyrans are based on the following core structure:

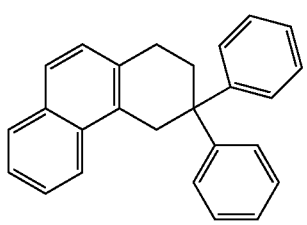 [SMILES: c1ccc(C2(c3ccccc3)CCc3ccc4ccccc4c3C2)cc1]

Exemplary naphthopyrans, including those that fluoresce, are described by Nunzio et al. (Chem. Phys. Chem. 9, 768-775 (2008)) and include, 2-(4'-piperidinophenyl)-2-phenyl-5-carbomethoxy-9-dimethylamino-2H-naphtho [1,2-b]pyran (NP-1), and 2-(4'-dimethylaminophenyl)-2-(4'''-methoxyphenyl)-5-hydroxymethyl-9-pyrrolidino-2H-naphtho [1,2-b]-pyran (NP-2) as shown below:

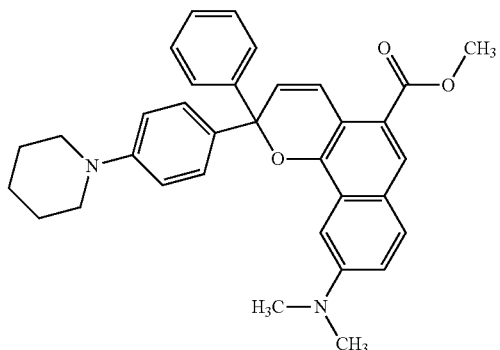

NP-1

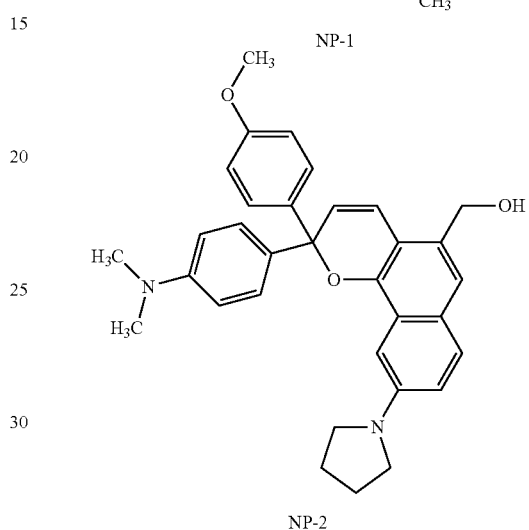

NP-2

NP-1 and NP-2 naphthopyrans displayed fluorescence with wavelengths ($\lambda_{max}$) of 577 nm and 550 nm, respectively.

Naphthopyrans have also been modified with a second photochrome. For example, Delbaere et al. (Org. Lett. 8:4931-4934 (2006)) describes a hybrid naphthopyran-dithienylethene compound. The photochemistry of eight different isomers was explored. Irradiation with 365 nm light gives rise to the thermally reversible opening of naphthopyran ring. Irradiation at 313 nm leads to the closure of the dithienylethene moiety and the opening of the naphthopyran group, generating seven different structures in different concentrations.

Another photochrome type is diarylethene. A diarylethene photochrome can be very useful in a biocompatible polymer of the invention because of their thermal irreversibility, sensitivity and fatigue resistance. Diarylethenes are based on the following core structure:

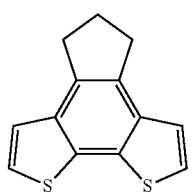 [SMILES: c1cc2c3c(c4ccsc4c2s1)CCC3]

Exemplary diarylethene derivatives, including ones that fluoresce, are described by Cipolloni et al. (J. Phys. Chem. 112, 4765-4771 (2008)). Cipolloni's diarylethenes include 3,4-bis(2-methylbenzo[b-]thiophen-3-yl)-1,1-dimethyl-2,5- dihydro-1H-silole (BTSi), 3,4-bis(2,5-dimethylthien-3-yl)-1,1-dimethyl-2,5-dihydro-1Hsilole(TSi), 3,4-bis(2-methylbenzo [b]thiophen-3-yl)-1-phenyl-2,5-dihydrophosphole 1-oxide (BTPO) and 3,4-bis(2,5-dimethylthien-3-yl)-1-phenyl-2,5-dihydrophosphole 1-oxide (TPO). Diarylethenes described by Cipolloni have a Si atom or a PO group in the pentatomic ring which fixes the compounds in the cis conformation. BTSi and BTPO diarylethenes in the closed ring isomeric form displayed fluorescence with wavelengths ($\lambda_{max}$ ($\Phi_F$)) of 575 nm and 570 nm, respectively.

Another fluorescent diarylethene derivative described by Cusido et al. (Eur. J. Org. Chem. 2031-2045 (2009)) is an emissive tungsten complex combined with a dirarylethene through a pyridyl ligand (see also Fernández-Acebes and Lehn (1998) *Adv. Mater.* 10, 1519-1522; and Fernández-Acebes and Lehn (1999) *Chem. Eur. J.* 5, 3285-3292).

Other exemplary diarylethenes include those that are coupled to a fluorescent molecule. Diarylethenes-based fluorescent chromophore derivatives are described by Yagi et al. (J. Org. Chem. 66, 5419-5423 (2001)). In particular, Yagi describes the synthesis coupling various diarylethene species to a fluorescent 2,4,5-triphenylimidazole chromophore. Upon excitation of the triphenylimidazole chromophore with 366 nm light, the derivatives underwent photocyclization reactions, and the solutions containing the derivatives changed color from colorless to red-purple or to blue. The colors disappeared by irradiation with visible ($\lambda$>480 nm) light. The fluorescence intensity of the solutions also reversibly changed with the photochromic reactions.

Another photochrome type is azobenzene. Azobenzene photochromes are based on the following core structure:

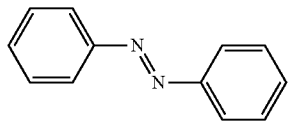 [SMILES: c1ccc(/N=N/c2ccccc2)cc1]

Another photochrome type is a coumarin derivative. Coumarin photochromes are based on the following core structure:

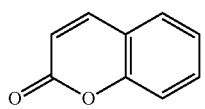 [SMILES: O=c1ccc2ccccc2o1]

Exemplary coumarin derivatives, including ones that fluoresce, are described by Traven et al. (Organic Letters 10, 1319-1322 (2008)) and include compounds of the following formula:

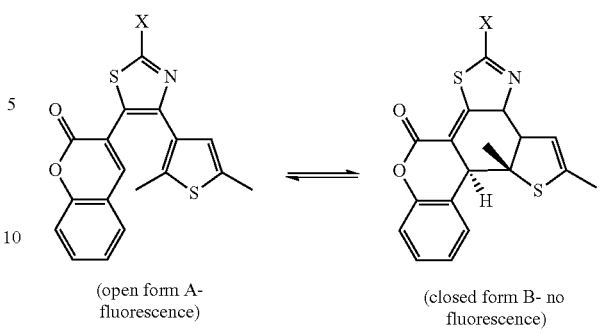

wherein X is —CH$_3$, -Ph, -4-OMeC$_6$H$_4$, —NH$_2$, or NHPh. These compounds display intensive fluorescence emission in the open form A, which is modulated by light. Fluorescence intensity decreases significantly upon irradiation of A with UV-light ($\lambda$<400 nm) due to formation of the cyclic form B. Irradiation of B with visible light ($\lambda$>470 nm) promotes its opening and the recovering of fluorescence.

Near infrared (IR) dyes are compounds capable of absorbing electromagnetic radiation and emitting electromagnetic radiation in the near IR range. Typically near IR dyes absorb in the visible (400-700 nm) and/or near IR range (700-1000 nm) of the electromagnetic spectrum, and more typically in the range of about 650 to about 800 nm. Near IR emission is also typically in the range of about 650 to about 800 DM. Exemplary near IR dyes include benz(indolium) derivatives; cyanines including hydrocyanines, tricarboxycyanines, and indocyanines; squaraines and rotaxanes; and oxazines.

One class of near IR cyanine dyes are based on the following formula:

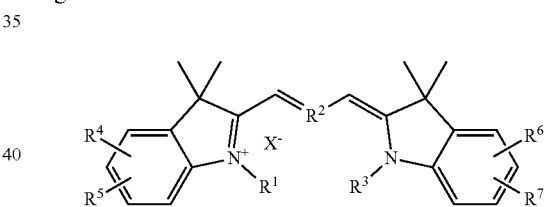

In this formula, R$^1$ and R$^3$ are independently selected from hydrocarbon-containing groups, unsubstituted or substituted with heteroatoms, including halogens, charged groups, or salts, or combinations thereof. In some cases, R$^1$ and R$^3$ represent spacer groups to which the cyanine dye can be attached to the polymer. In some aspects, R$^1$ and R$^3$ are independently selected from linear or branched alkyl, with optional heteroatom, such as halogen substitution. In some preferred aspects, R$^1$ and R$^3$ are independently selected from —R$^8$R$^9$, wherein R$^8$ is —(CH$_2$)$_x$—, wherein x is an integer in the range of 1-10, preferably 1-6, and R$^9$ is selected from —CH$_3$, an anionic group such as —CO$_2$ and —SO$_3^-$, —OH, a nucleophilic group such as —NH$_3$, and acids and salts thereof.

R$^2$ can be a saturated, unsaturated, or partially saturated divalent hydrocarbon-containing group, such as a linear, branched, aromatic or non-aromatic cyclic divalent hydrocarbon group unsubstituted or substituted with heteroatoms, including halogens and/or salts. In some aspects R$^2$ is selected from —(CH$_n$)$_m$—, wherein n is 1 or 2, and m is an integer in the range of 1-8, or 1-4. In other aspects, R$^2$ is —R$^6$—, wherein R$^6$ is a saturated, partially saturated, or unsaturated cyclic hydrocarbon group (such as C6) with optional substitution.

$R^4$, $R^5$, $R_6$, and $R^7$ are optional, and can be independently selected from —H, short chain alkyl (e.g., —CH$_3$ or —CH$_2$CH$_3$), and halogen (e.g., —Cl, —Br, —F), or $R^4$ and $R^5$, and/or $R^6$ and $R^7$ can be covalently bonded to from a fused ring structure, such as an fused aromatic group (e.g., aryl), which optionally can be further substituted.

X is a suitable anionic atom or compound, such as, I$^-$, Br$^-$, and Cl$^-$.

Exemplary near IR cyanine dyes include:

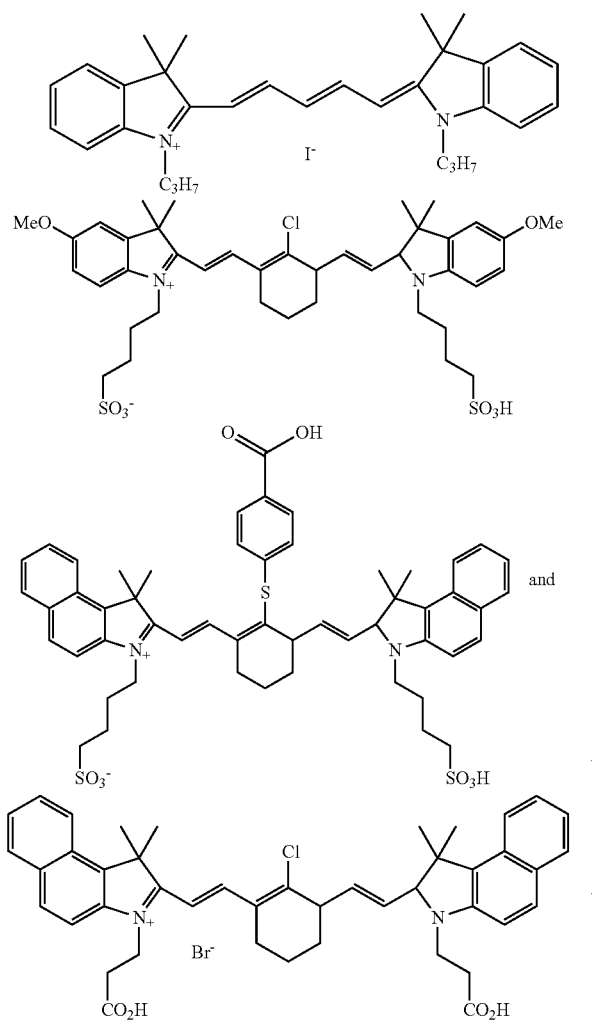

Another class of near IR dyes is benz[e]indolium dyes based on the following formula:

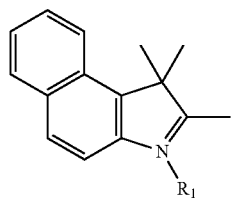

In this formula, $R^1$ is a hydrocarbon-containing group, unsubstituted or substituted with heteroatoms, including halogens, charged groups, or salts, or combinations thereof.

In some cases, $R^1$ represents a spacer groups to which the benz[e]indolium dye can be attached to the polymer. In some aspects, $R^1$ is a linear or branched alkyl, with optional heteroatom, such as halogen substitution. In some preferred aspects, $R^1$ is —$R^8R^9$, wherein $R^8$ is —(CH$_2$)$_x$—, wherein x is an integer in the range of 1-10, preferably 1-6, and $R^9$ is selected from —CH$_3$, an anionic group such as —CO$_2^-$ and —SO$_3^-$, —OH, a nucleophilic group such as —NH$_3$, and acids and salts thereof.

Exemplary benz[e]indolium dyes include:

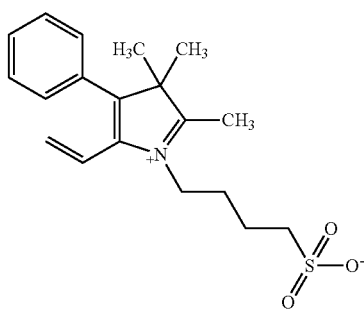 [SMILES: C=CC1=C(c2ccccc2)C(C)(C)C(C)=[N+]1CCCCS(=O)(=O)[O-]]

1,1,2-Trimethyl-3-(4-sulfobutyl)-1H-benz[e]indolium hydroxide, inner salt

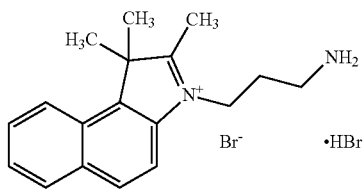 [SMILES: CC1=[N+](CCCN)c2ccc3ccccc3c2C1(C)C ; [Br-] ; Br]

1-(3-Aminopropyl)-2,3,3-trimethyl-4,5-benzindolium bromide hydrobromide

Another class of near IR dyes is tricarbocyanine dyes based on the following formula:

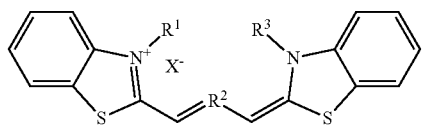

In this formula, $R^1$ and $R^3$ are independently selected from hydrocarbon-containing groups, unsubstituted or substituted with heteroatoms, including halogens, charged groups, or salts, or combinations thereof. In some cases, $R^1$ and $R^3$ represent spacer groups to which the tricarbocyanine dye can be attached to the polymer. In some aspects, $R^1$ and $R^3$ are independently selected from linear or branched alkyl, with optional heteroatom, such as halogen substitution. In some preferred aspects, $R^1$ and $R^3$ are independently selected from —$R^4R^5$, wherein $R^4$ is —(CH$_2$)$_x$—, wherein x is an integer in the range of 1-10, preferably 1-6, and $R^5$ is selected from —CH$_3$, an anionic group such as —CO$_2$ and —SO$_3^-$, —OH, a nucleophilic group such as —NH$_3$, and acids and salts thereof.

$R^2$ can be a saturated, unsaturated, or partially saturated divalent hydrocarbon-containing group, such as a linear, branched, aromatic or non-aromatic cyclic divalent hydrocarbon group unsubstituted or substituted with heteroatoms, including halogens and/or salts. In some aspects $R^2$ is selected from —$(CH_n)_m$—, wherein n is 1 or 2, and m is an integer in the range of 1-8, or 1-4. In other aspects, $R^2$ is —$R^6$—, wherein $R^6$ is a saturated, partially saturated, or unsaturated cyclic hydrocarbon group (such as C6) with optional substitution.

Exemplary tricarbocyanine dyes include:

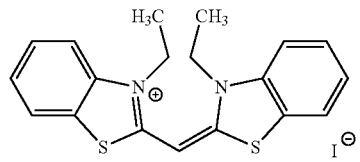 [SMILES: CCN1/C(=C\c2sc3ccccc3[n+]2CC)Sc2ccccc21 ; [I-]]

3,3'-diethylthiacyanine iodide, and

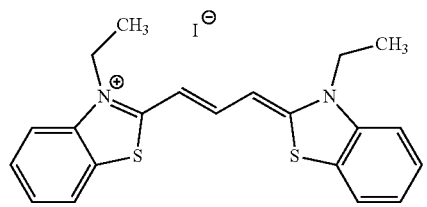 [SMILES: CCN1/C(=C/C=C/c2sc3ccccc3[n+]2CC)Sc2ccccc21 ; [I-]]

3,3'-diethylthiacarbocyanine iodide.

Another class of near IR dyes is squarane dyes which are based on the following formula:

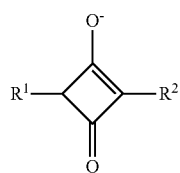

Wherein $R^1$ and $R^2$ generally each individually include a group selected from electron rich aromatic, heteroaromatic, and olefinic groups. More specific examples of squarane dyes include:

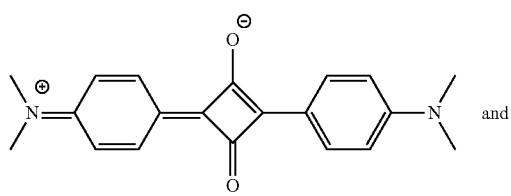

and

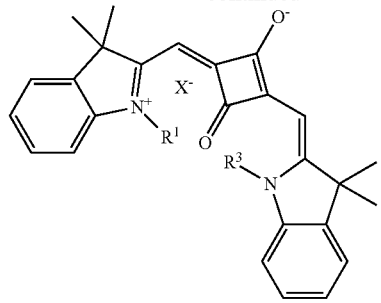

In this formula, $R^1$ and $R^3$ are independently selected from hydrocarbon-containing groups, unsubstituted or substituted with heteroatoms, including halogens, charged groups, or salts, or combinations thereof. In some cases, $R^1$ and $R^3$ represent spacer groups to which the squarane dye can be attached to the polymer. In some aspects, $R^1$ and $R^3$ are independently selected from linear or branched alkyl, with optional heteroatom, such as halogen substitution. In some preferred aspects, $R^1$ and $R^3$ are independently selected from —$R^4R^5$, wherein $R^4$ is —$(CH_2)_x$—, wherein x is an integer in the range of 1-10, preferably 1-6, and $R^5$ is selected from —$CH_3$, an anionic group such as —$CO_2^-$ and —$SO_3^-$, —OH, a nucleophilic group such as —$NH_3$, and acids and salts thereof. The synthesis of water soluble squarane dyes is described in, for example, Tatarets et al. (Analytica Chimica Acta, 570:214 (2006)).

Another class of near IR dyes is oxazine dyes which are based on the following formula:

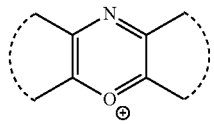

in which the oxazine ring is fused to two or more aromatic groups, which in turn can be further fused to other cyclic groups, or ring substituted.

Exemplary oxazine dyes include:

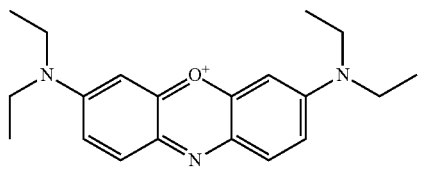 [SMILES: CCN(CC)c1ccc2nc3ccc(N(CC)CC)cc3[o+]c2c1]

3,7-bis(diethylamino)phenoxazin-5-ium perchlorate

The polymer can also be coupled to a rotaxane. A rotaxane is composed of an elongated molecule with bulky chemical ends (and such as having near a fluorescence properties) that is threaded through a macrocycle resulting in a mechanically-interlocked molecular architecture. Dyes that include this interlocked architecture can demonstrate increased stability of the dye molecule. Exemplary rotaxanes include cyclodextrin protected azo dyes. Squaraine-based rotaxanes dyes have enhanced stability achieved by preventing nucleophilic attack of the inner squaraine moiety. The enhanced stabilities of rotaxane dyes are attributed to the insulating effect of the macrocycle which is able to block interactions with other molecules.

In general, a photochrome-containing polymer is one wherein one or more photochrome moiety or moieties is covalently bonded to a portion of the polymer. Likewise, a near IR dye-containing polymer is one wherein one or more near IR dye moiety or moieties is covalently bonded to a portion of the polymer. The photochrome or near IR dye moiety can be "pendent" from the polymer backbone of a photochrome- or near IR dye-containing polymer. In other words, a pendent photochrome or near IR dye moiety is presented as a branch structure extending from a monomeric unit of the polymeric backbone. The pendent photochrome or near IR dye moiety can be spaced away from the monomeric unit of the polymer backbone by a spacer group as described herein.

The photochrome- or near IR dye-containing polymer can be prepared by any one of a variety of methods. For example, in one mode of preparation, a photochrome- or near IR dye-containing polymerizable monomer is first synthesized or obtained. The photochrome- or near IR dye-containing polymerizable monomer is then co-polymerized with other monomers, or combinations of other monomers.

Polymerization of the photochrome- or near IR dye-containing polymerizable monomer into a polymer can be carried out by various polymerization techniques, including addition polymerization and condensation polymerization. Addition polymerization, such as free radical polymerization, is a preferred mode of incorporating a photochrome- or near IR dye-containing polymerizable monomer into the polymer.

In some modes of practice, the photochrome- or near IR dye-containing polymerizable monomer includes an ethylenically unsaturated group. An ethylenically unsaturated group can be found on acrylate-based monomers such as acrylate, methacrylate, hydroxyethyl methacrylate, dipropyleneglycol monoacrylate, diethyleneglycol monoacrylate, ethacrylate, 2-phenyl acrylate; acrylamide-based polymers such as acrylamide and methacrylamide; and itaconate, and styrene. In some modes of practice, a photochrome- or near IR dye-containing polymerizable monomer can be formed by the synthesis of a compound containing a photochrome or near IR dye moiety with a compound containing an ethylenically unsaturated group, including those described herein. As such, the polymeric backbone group of the polymer formed from the polymerization of the photochrome- or near IR dye-containing polymerizable monomer can be acrylate-containing, acrylamide-containing, etc., according to the monomer types that are use to form the photochrome- or near IR dye-containing polymerizable monomer.

A photochrome-containing polymerizable monomer can be synthesized using various reaction schemes. In one mode of practice, in a first step, a compound representing a portion of the photochrome moiety is reacted with a compound that provides the spacer group in the monomer to provide a first intermediate compound. In this first step, one mechanism involves nucleophilic substitution using the heteroatom in the photochrome moiety. The compound that provides the spacer group can include a halide as the leaving group, which can be reacted with a nitrogen heteroatom in the photochrome ring. In a second step, the first intermediate compound is reacted with a compound that completes the photochrome moiety, thereby producing a second intermediate compound. In a third step, the second intermediate compound is reacted with a compound that provides a polymerizable group.

An exemplary synthesis scheme for a spiropyran-based monomer is shown below, which shows the first step which is the reaction of 2,3,3-trimethyl-3H-indole (compound A) with bromomethyl benzoic acid (compound B) in the presence of acetonitrile (ACN). This provides the first intermediate compound (C) that includes a portion of the photochrome moiety and the spacer group.

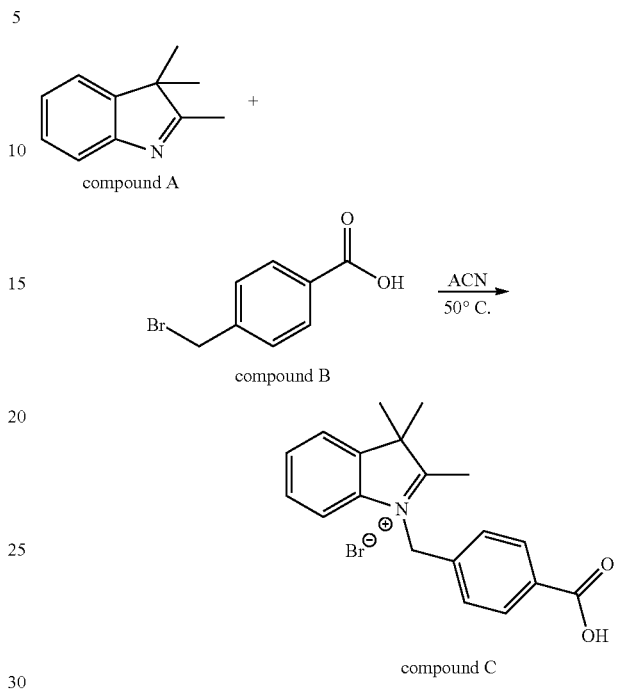

As an alternative, and to provide a different spacer group chemistry, compound B can be replaced with a different halogenated acid, such as one of formula I: $X^1$—$R^1$—COON, wherein $X^1$ is a halogen selected from Br, Cl, and I, and $R^1$ is a hydrocarbon-containing group. Exemplary hydrocarbon-containing groups include saturated, unsaturated, or partially saturated linear, cyclic, or branched hydrocarbon-containing divalent radicals, such as ones having from 2-18 carbons, and more preferably 4-16 carbons.

Next, intermediate compound C is reacted with 2-hydroxy-5-nitro-benzaldehyde (compound D) in the presence of triethylamine (NEt$_3$) to complete the photochrome moiety, thereby providing the second intermediate compound (E).

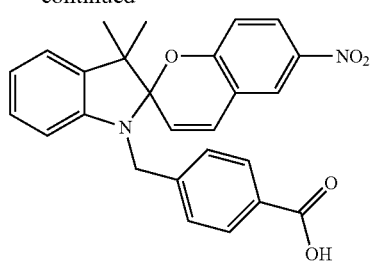

compound E

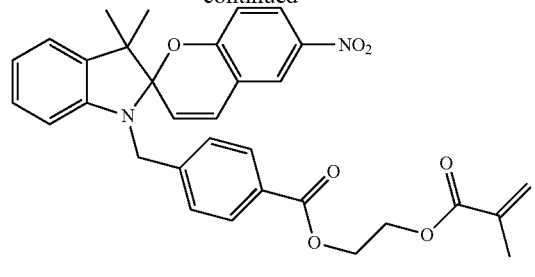

compound G

As an alternative, and to provide a different spiropyran species as the photochrome moiety, compound D can be replaced with a different benzaldehyde compound, such as one of the formula II:

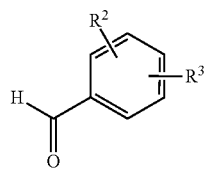

In some aspects, both of $R^2$ and $R^3$ are H. In other aspects, one or both of $R^2$ and/or $R^3$ are independently selected from electron withdrawing groups, such as nitro (—$NO_2$), quaternary amine, trihalide, cyano, sulfonate, carboxylic acid, and ester, wherein if $R^2$ or $R^3$ is not an electron withdrawing group, then it is H.

Next, intermediate compound E is reacted with ethyleneglycol monoacrylate (compound F) in the presence of DIC (diisopropylcarbodiimide) and DMAP (4-(dimethylamino) pyridine)) under basic conditions to provide the final compound (G) which is a photochrome-coupled monomer.

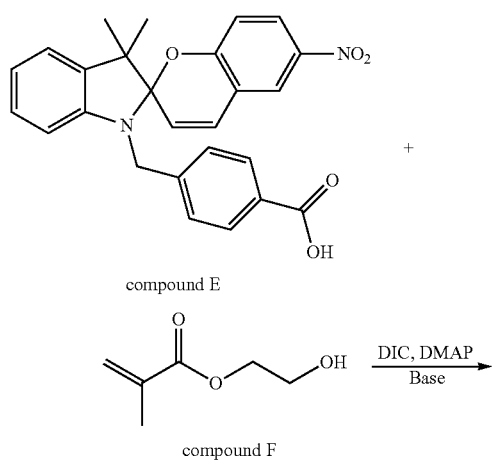

compound E compound F

As an alternative, and to provide a different monomer chemistry (which can affect the nature of the polymer backbone), compound F can be replaced with a different compound including an ethylenically unsaturated group and carboxylate-reactive group, such as a hydroxyl group. For example, the compound F can alternatively be selected from hydroxyethyl methacrylate, propyleneglycol monoacrylate, dipropyleneglycol monoacrylate, or diethyleneglycol monoacrylate.

In some aspects the biocompatible photochrome-containing polymer includes a monomeric unit of formula III:

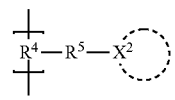

wherein $R^4$ is a group of the polymeric backbone, $R^5$ is a spacer group, and $X^2$ is N, which is a heteroatom in a ring structure in the photochrome moiety.

With regards to the polymeric backbone the biocompatible photochrome-containing polymer, in more specific aspects, $R^4$ is according to sub-formula IIIa:

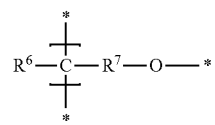

wherein $R^6$ is H or $CH_3$, and $R^7$ is a covalent bond, —$(CH_2)_n$—, wherein n is an integer in the range of 1 to 3, —C(O)O—$R^8$—, wherein $R^8$ is —$(CH_2)_m$—, wherein m is an integer in the range of 1 to 3.

With regards to the photochrome moiety, in more specific aspects, the monomeric unit can have the following formula IV:

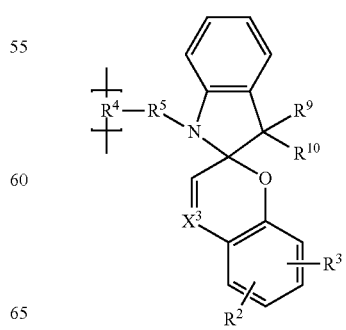

wherein $R^4$ is a group of the polymeric backbone, $R^5$ is a spacer group, $R^9$ and $R^{10}$ are independently selected from —H and —$CH_3$, $X^3$ is N or C, and $R^2$ and/or $R^3$ are independently selected from electron withdrawing groups, such as nitro (—$NO_2$) quaternary amine, trihalide, cyano, sulfonate, and carboxylic acid, and ester, wherein if $R^2$ or $R^3$ is not an electron withdrawing group, then it is H.

In some aspects $R^4$ is a group selected from acrylate, methacrylate, hydroxyethyl methacrylate, dipropyleneglycol monoacrylate, diethyleneglycol monoacrylate, ethacrylate, acrylamide, methacrylamide, and itaconate radicals. In some aspects $R^5$ is a divalent spacer group comprising a linear, branched, or cyclic hydrocarbon group.

Near IR dye-containing hydrophilic polymers can be prepared by methods including covalently bonding a near IR dyes to a hydrophilic preformed polymer, and by co-polymerizing a near IR dye-containing monomer with one or more other hydrophilic monomers. Some modes of synthesis involve a step of reacting a near a dye including a primary amine-reactive group with a preformed polymer or monomer bearing an amine group. In some modes of practice, NHS-modified near IR dyes can be obtained or prepared. Near IR dyes including a carboxylate group, such as those described herein, can be reacted with NHS(N-hydroxysulfosuccinimide) in the presence of EDC (1-Ethyl-3-[3-dimethylaminopropyl]carbodiimide hydrochloride). EDS creates an o-acylisourea ester dye intermediate, which is then replaced with the NITS group. The NHS-modified near IR dye is then reacted with a primary amine-bearing monomer or preformed polymer. Exemplary primary amine-bearing monomer or preformed polymers include aminopropylmethacrylamide (APMA).

An exemplary NITS-modified cyanine near IR dye is shown below:

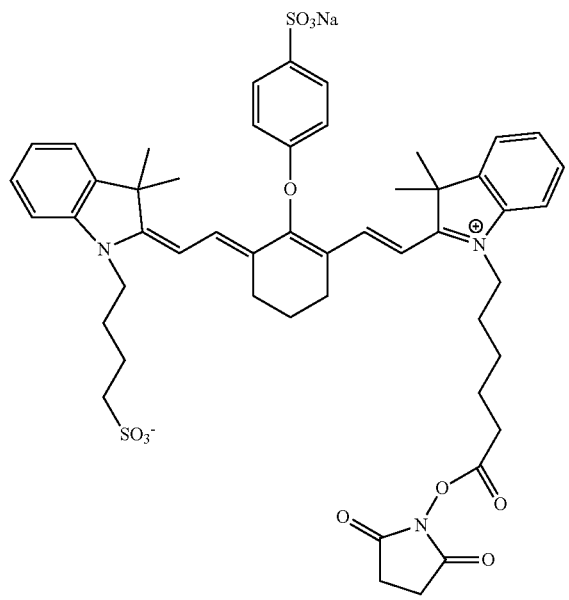

and commercially available from LI-COR Biosciences (Lincoln, Nebr.).

In order to prepare a photochrome- or near IR dye-containing polymer, a photochrome- or near IR dye-containing monomer can be copolymerized with one or more other monomers. For purposes of discussion, monomers in the polymerization mixture may be referred to as a "first monomer," "second monomer," etc. For example, a polymerization mixture can include a first monomer comprising a photochrome or near IR dye moiety, a second monomer that is hydrophilic, and optionally a third monomer comprising a fluorescence moiety.

The amount of photochrome- or near IR dye-containing monomer used in the polymerization mixture can be expressed by the weight percent of the monomer in the mixture, or by the molar quantity of the photochrome or near a dye moiety as provided by the monomer in the polymerizable material. As a general matter, visually useful photochrome- or near IR dye-containing polymers can be prepared with very small amounts of the photochrome or near IR dye moiety present in the polymer. For example, in some aspects the amount of photochrome or near IR dye moiety present may be as low as about 0.05 mol % of polymer, or even about 0.01 mol % of polymer. Exemplary ranges of photochrome or near IR dye moiety can be in the range of about 0.1 mol % to about 25 mol % of polymer, or more specifically about 1 mol % to about 10 mol % of polymer.

The photochrome- or near IR dye-containing polymer can be prepared with an amount and type of polymer forming material (monomers) to provide a desired hydrophile balance. In some aspects, the photochrome- or near IR dye-containing polymer can be prepared to have hydrophilic properties. As used herein, a polymer having "hydrophilic" properties can be soluble in water. Accordingly, a coating prepared from a hydrophilic polymer can be wetted and retain water. The hydrophilicity of a polymer can be described in terms of how soluble the polymer is in water; likewise, a coating can be described in terms of the amount of water the coating can retain when wetted. In some aspects, the photochrome- or near IR dye-containing polymer has a solubility in water of about 0.5 mg/mL or greater, about 1 mg/mL or greater, about 5 mg/mL or greater, or about 10 mg/mL or greater. Highly water-soluble photochrome- or near IR dye-containing polymers of the invention may have a solubility up to about 500 mg/mL or greater.

Along with the photochrome- or near IR dye-containing monomer, one or more other monomers that do not include a photochrome or near IR dye moiety can be included in the polymerization mixture to form the photochrome- or near IR dye-containing polymer. In many aspects the monomer that does not include a photochrome or near IR dye moiety can be a free-radically polymerizable monomer. Examples of free radically polymerizable hydrophilic monomers include acrylic monomers such as acrylic acid, methacrylate, methyl methacrylate, hydroxyethyl methacrylate, hydroxyethyl acrylate, methacrylic acid, acrylic acid, glycerol acrylate, glycerol methacrylate; and acrylamide-based monomers such as acrylamide, methacrylamide, aminopropylmethacrylamide, and derivatives and/or mixtures of any of these. Other hydrophilic monomers include, for example, methyl vinyl ether, maleic anhydride, vinyl pyrrolidone, and mixtures of any of these.

A hydrophilic monomer that does not include a photochrome or near IR dye moiety, or a combination of these types of hydrophilic monomers, can be used as the primary monomer in the polymerizable composition. In other words, it is used in an amount greater that any other monomer in the composition. In some aspects the hydrophilic monomer that does not include a photochrome or near IR dye moiety is used in the polymerizable composition in an amount of 5% wt or greater, such as in the range of about 10% wt to about 90% wt, about 25% wt to about 80% wt, or about 50% wt to about 75% wt.

In some aspects, the polymerization mixture can include one or more monomer(s) that increase the photochrome- or near IR dye-containing polymer's solubility in polar protic solvents, such as alcohols like butanol, isopropanol, n-propanol, ethanol, and methanol, or polar aprotic solvents like acetone and ethyl acetate. Exemplary monomers include those having hydrophobic moieties such as dimethylacrylamides, diisopropylacrylamides, tert-butylacrylamides, and medium chain (e.g., C—C) alkyl acrylamides. A composition including the photochrome-containing polymer and a polar protic or aprotic solvent can be useful for coating substrates formed from silicone or other polymers on which water does not sheet out well.

In another aspect, the biocompatible photochrome- or near IR dye-containing polymer includes a polymeric backbone, a pendent photochrome or near IR dye moiety bonded to the polymer backbone, and a pendent fluorescence moiety, which may or may not be photochromic. In some aspects, a photochrome-containing polymer can be prepared by copolymerizing the photochrome-containing monomer with a monomer bearing a fluorescence moiety. The fluorescence moiety is able to absorb light and emit light of a different wavelength, with the emitted light generally having a longer wavelength (and therefore lower energy), than the absorbed radiation. The photochrome group has an emission spectrum that overlaps with the absorption spectrum of the fluorescence moiety when the photochrome moiety is in the transformed state.

In some aspects, a polymer is prepared using a photochrome that, when in a transformed state transfers energy to the fluorescence moiety, and allows visualization of the polymeric matrix by fluorescence.

Fluorescence moiety-containing monomers are commercially available or can be prepared using techniques available to one of skill in the art. For example, various fluorescence moieties such as fluorescein, naphthalene, (trifluoromethyl) coumarin, and anthracene are commercially available as polymerizable derivatives (e.g., in acrylated, methacrylated, diacrylated forms) from, for example, Sigma Aldrich.

In one mode of practice, the polymerization mixture includes (a) a photochrome- or near IR dye-containing monomer, (b) a fluorescence moiety-containing monomer, and (c) a monomer that does not include a photochrome, near IR dye, or fluorescence moiety. Exemplary ranges for the components in the polymerizable composition are as follows: (a) photochrome- or near IR dye-containing monomer at about 1% wt to about 50% wt, (b) fluorescence moiety-containing monomer at about 1% wt to about 50% wt, and (c) monomer that does not include a photochrome, or near IR dye, or fluorescence moiety at about 1% wt to about 99% wt.

In some modes of practice, a polymer is prepared with a photochrome-containing monomer is located proximal to a fluorescence moiety-containing monomer in the polymer.

Optionally, the photochrome- or near IR dye-containing polymer can be prepared with a hydrophilic monomer that provides a pendent charged group. For example, a monomer providing a negatively charged group such as sulfonate or phosphonate can optionally be included in the photochrome- or near IR dye-containing polymer. An exemplary sulfonate-containing monomer is 2-acrylamido 2-methyl propane sulfonate (AMPS). As another option, a monomer that provides a positively charged group such as quaternary ammonium, quaternary phosphonium, or ternary sulfonium groups can be used in the photochrome-containing polymer. An exemplary ammonium-containing monomer is (3-acrylamidopropyl)-trimethylammonium chloride (APTAC; Simga-Aldrich Corp., St. Louis, Mo.).

In some modes of synthesis, a photochrome- or near IR dye-containing polymer is synthesized by first preparing or obtaining a pre-polymer having a pendent reactive group(s), and then reacting the pre-polymer with a photochrome—or near IR dye-containing compound. In some modes of synthesis, the pendent reactive group(s) can be in the form of a hydroxyl group, which is reactive with a hydroxyl-reactive group present on a photochrome moiety. For example, a hydrophilic co-polymer can be prepared including at least two hydrophilic monomer types, the first hydrophilic monomer being a non-hydroxylated hydrophilic monomer, and the second monomer being a hydroxylated hydrophilic monomer. The amount of hydroxylated hydrophilic monomer present can control the loading of the photochrome moiety on the polymer. As an example, a vinyl pyrrolidone (90%)-hydroxymethyl acrylate (10%) copolymer is prepared using free radical polymerization. The polymer is then reacted with compound E (as described herein) in excess, which results in the reaction between the hydroxyl and carboxylate groups, and coupling of the photochrome moiety to the backbone of the polymer.

In another mode of synthesis, a NHS-modified near IR dye is reacted with a primary amine-group on a preformed polymer, such as a preformed polymer that includes aminopropylmethacrylamide (APMA).

The photochrome- or near IR dye-containing polymer can also include monomeric units bearing pendent photoreactive groups capable of being activated by UV radiation and undergoing covalent bonding to a target group (herein referred to as "latent reactive photogroups"). Such photochrome- or near IR dye-containing polymers with a photoreactive group can be treated with actinic radiation to activate the photogroup to a radical species which is then able to react with a target component and promote stabilization of the photochrome-containing polymers in the treated composition. For example, a coating composition including the photochrome- or near IR dye-containing polymer can be treated with UV radiation to cause covalent crosslinking of the polymer in the composition, and/or covalent immobilization of the polymer to a device surface via the reacted photogroup. The covalent bonding as caused by activation of the photoreactive group can improve the stability of the coating components and can provide a coating with improved durability.

A "latent reactive photogroup," as used herein, refers to a chemical group that responds to applied electromagnetic energy in order to undergo active specie generation, resulting in covalent bonding to an adjacent chemical structure (via an abstractable hydrogen). "Photoreactive" or "latent" refers to those groups that are responsive to the electromagnetic energy but that have not yet been activated to undergo covalent bonding, whereas "photoreacted" or "reacted" refers to those groups that have been activated by electromagnetic energy and have undergone covalent bonding to a target moiety. A pretreated photochrome- or near IR dye-containing polymer or composition can be described using terminologies such as "photoreactive" or "latent" to appropriately describe the chemical nature of these groups. "Photoreacted" or "reacted" can be used to describe those polymers or compositions having undergone photoactivation resulting in covalent bonding of the photogroup to a target moiety.

Preferred latent reactive groups are sufficiently stable to be stored under conditions in which they retain such properties. See, for example, U.S. Pat. No. 5,002,582 (Guire et al). Latent photoreactive groups can be chosen that are responsive to various portions of the electromagnetic spectrum, with those responsive to ultraviolet and visible portions of the spectrum being particularly preferred.

Photoreactive species respond to a specific applied external ultraviolet or visible light source to undergo active specie generation with resultant covalent bonding to an adjacent chemical structure, for example, as provided by the same or a different molecule. Photoreactive species are those groups of atoms in a molecule that retain their covalent bonds unchanged under conditions of storage but that, upon activation by a specific applied external ultraviolet or visible light source form covalent bonds with other molecules. Photoreactive species generate active species such as free radicals and particularly nitrenes, carbenes, and excited states of ketones, upon absorption of electromagnetic energy.

Exemplary latent photoreactive groups are aryl ketones, such as acetophenone, benzophenone, anthraquinone, anthrone, and anthrone-like heterocycles (for example, heterocyclic analogs of anthrone such as those having nitrogen, oxygen, or sulfur in the 10-position), or their substituted (for example, ring substituted) derivatives.

Aryl ketones are preferred photoreactive moieties, since they are capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (for example, carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased bonding efficiency.

In one embodiment, a photoreactive group is pendent from a monomer in the photochrome- or near IR dye-containing polymer. In this sense the polymer includes at least two pendent groups which are different and that are capable of responding to light radiation: a first pendent group including the photochrome or near IR dye moiety, and a second pendent group containing a photogroup capable of being activated by UV irradiation and bonding to a target moiety.

The photoreactive group can be introduced into the photochrome- or near IR dye-containing polymer according to any one of various methods. For example, in one mode of practice a monomer is obtained or prepared having a photoreactive group. The monomer is then polymerized along with the photochrome- or near IR dye-containing monomer and one or more other monomers that do not include a photochrome or near IR dye moiety.

Exemplary monomers with photoreactive groups that can be incorporated into the photochrome- or near IR dye-containing polymer include those based on acrylamide and methacrylamide. One exemplary methacrylamide-based monomer with a pendent photoreactive groups is N-[3-(4-benzoylbenzamido)propyl]methacrylamide (BBA-APMA), the synthesis of which is described in Examples 1-3 of U.S. Pat. No. 5,858,653 (Duran et al.) Another exemplary methacrylamide-based monomer with a pendent photoreactive group is N-[3-(7-methyl-9-oxothioxanthene-3-carboxiamido)propyl]methacrylamide (MTA-APMA), the synthesis of which is described in Examples 1-2 of U.S. Pat. No. 6,156,345 (Chudzik et al.)

For photochrome- or near IR dye-containing polymers including a monomer with a pendent latent photoreactive group, the photochrome-containing polymer is synthesized to have at least one photoreactive group per polymer. More typically, the photochrome-containing polymer is prepared to provide a loading of the photoreactive group on the polymer in the range of about 0.01 mmol/g to about 1 mmol/g (mmol photoreactive group per gram of polymer), and more specifically in the range of about 0.1 mmol/g to about 0.5 mmol/g.

Alternatively, in another mode of practice, the photochrome- or near IR dye-containing polymer is prepared with a monomer having a group (e.g., a primary amine group) that can specifically react with a compound that has a photoreactive group and a corresponding reactive (e.g., amine reactive) group. For example, the photochrome- or near IR dye-containing polymer can be prepared with a monomer that presents a pendent amine group, such as N-(3-aminopropyl) methacrylamide, following its synthesis. An amount of monomer can be chosen to provide a desired level of loading of photoreactive groups following synthesis. Following its preparation, the photochrome- or near IR dye-containing polymer is then reacted with a photoreactive group-containing compound under conditions to promote covalent bonding to the amine group on the photochrome-containing polymer. An example of an amine-reactive photoreactive group-containing compound is 4-benzoylbenzoyl chloride, which can be reacted with a primary amine group pendent from the photochrome-containing polymer under Schotten-Baumann conditions (see, for example, Example 2 of U.S. Pat. No. 5,563,056 (Swan et al.))

Polymerization of monomeric material including the photochrome- or near IR dye-containing monomer and one or more other co-monomers is carried out under standard reaction conditions. One or more solvents can be chosen for the polymerization composition based on the solubility profiles of the various monomers. Exemplary solvents for polymerization include water and organic solvents. In one mode of practice polymerization is carried out in a composition using DMSO as the solvent. In another mode of practice, polymerization is carried out in a composition using water, THF and ethanol. Liquid mixtures like these can be used as a solvent system to accommodate for the copolymerization of monomers that have little or no appreciable solubility in water. Total monomer concentration in the polymerization composition typically ranges from about 1% wt to about 20% wt, and more specifically from about 5% wt to about 10% wt.

In one mode of practice, free radical polymerization of the desired monomers is performed. Since the photochrome- or near IR dye-containing polymer will have at least one group affected by light (i.e., at least the photochrome or near IR dye group), one preferred polymerization initiator system is based on redox components. Exemplary redox polymerization initiators include ammonium persulfate (APS), 2-azobis (isobutyro-nitrile), potassium persulfate, and organic peroxides, including hydroperoxides, for example alkyl hydroperoxides, such as para-menthane, t-butyl hydroperoxide, and t-butyl perbenzoate. Co-initiators, such as tetramethylethylenediamine (TEMED) can be used.

The polymerization composition can be deoxygenated by sparging with an inert gas such as helium or nitrogen. Polymerization can be carried out at temperatures in the range of about 25° C. to 80° C. After polymerization is complete, the photochrome- or near IR dye-containing polymer can be isolated by addition of a non-solvent or through dialysis in water or other polar solvents.

A photochrome- or near IR dye-containing polymer can optionally be prepared having a pendent polymerizable group. Typically, the polymerizable group is added to a formed polymer. For example, a formed photochrome- or near IR dye-containing polymer can be prepared having, in addition to the pendent photochrome or near IR dye group, an amine-bearing pendent group. The pendent amine group on the polymer can then be reacted with a compound that provides an ethylenically unsaturated group, such as acryloyl chloride. The amount loading of the pendent amine group can dictate the loading of the polymerizable group. U.S. Pat. No. 6,410,044 (Chudzik et al.) describes the reaction of acryloyl chloride with amine-bearing polymer for the formation of macromers (see Examples 10 and 11).

Photochrome- or near IR dye-containing macromers can be polymerized to a polymeric matrix. A composition containing a photochrome- or near IR dye-containing macromer generally includes a polymerization initiator, or the photochrome-containing macromer is mixed with an initiating system to promote matrix formation. A polymeric matrix can be in various forms, such as an in situ-formed matrix, or the matrix can be associated with a medical device such as in the form of a coating, an overcoat, or a filler.

Compositions of the invention, e.g., coating or in-situ matrix forming compositions, can include the photochrome- or near IR dye-containing polymer of the invention, and optionally one or more other polymeric materials, that are suspended or dissolved in a solvent. Optionally, other materials, such as other non-polymeric materials, bioactive agents or compounds that can be used to promote polymeric matrix formation, can be included in the composition.

In some modes of practice, the composition including the photochrome- or near IR dye-containing polymer has a concentration of polymeric material in the range of about 5 mg/mL to about 100 mg/mL, or more specifically about 10 mg/mL to about 60 mg/mL. The amount of polymeric material in the composition can correspond to the photochrome- or near IR dye-containing polymer alone, or used in combination with one or more other different polymers. If more than one polymer is present in the first coating composition, the combined amount of polymeric materials can be in the ranges as described.

If the photochrome- or near IR dye-containing polymer includes a pendent polymerizable group (e.g., a photochrome- or near IR dye-containing macromer), the composition can include at least a polymerization initiator. Exemplary polymerization initiators for macromer-containing compositions include those described herein (e.g., redox polymerization initiators), as well as light activated initiators, especially those that may have an excitation wavelength that is different than the wavelength that causes transformation of the pendent photochrome or near IR dye moiety.

Exemplary biocompatible light activated photoinitiation systems for in-situ matrix forming compositions include water-soluble camphorquinone as described in U.S. Pub. No. 2006/0287410 (Chudzik, et al.). The composition can optionally include polymerization co-initiators, such as reducing agents, and/or polymerization accelerants (see, for example, U.S. Pub. No. 2005/0112086; Swan et al.). UV-activatable polymerization initiators, which can also be used as crosslinking agents, are described in this application in further detail below.

Optionally, the composition includes a photoreactive group present on a non-polymeric compound, such as a crosslinking agent. The photogroup(s) in the crosslinking agent can crosslink polymeric material together in a composition, or to another material, such as the material on a device surface. The crosslinked polymeric material can be crosslinked photochrome- or near IR dye-containing polymers, or a photochrome- or near IR dye-containing polymer crosslinked to one or more other (secondary, tertiary, etc.) polymer(s) in the composition. Depending on how the photochrome- or near a dye-containing polymer containing composition is used, the crosslinking agent can also bond the photochrome- or near IR dye-containing polymer to a material of a device surface. The bonding can improve coating properties, such as durability.

An example of a simple crosslinking agent is benzophenone, which has solubility in solvents such as tetrahydrofuran and ethanol.

In some cases, the composition includes a crosslinking agent that includes two or more photoreactive groups. The crosslinking agent can be ionic and soluble in an aqueous composition. An exemplary ionic photoactivatable crosslinking agent is a compound of formula V:

where Q is a radical containing at least one acidic group, basic group, or a salt of an acidic group or basic group. $R^{11}$ and $R^{12}$ are each independently a radical containing a latent photoreactive group.

The photoreactive groups can be the same as those described herein. Spacers can also be part of $R^{11}$ and $R^{12}$ along with the latent photoreactive group. In some embodiments, the latent photoreactive group includes an aryl ketone or a quinone. The radical Q in formula V provides the desired water solubility for the ionic photoactivatable cross-linking agent.

In some cases, Q is a radical containing at least one acidic group or salt thereof. Such a photoactivatable cross-linking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic cross-linking agent includes a sulfonic acid or sulfonate group. Suitable counter ions include alkali, alkaline earths metals, ammonium, protonated amines, and the like.

A compound of formula V can have a radical Q that contains a sulfonic acid or sulfonate group; $R^{11}$ and $R^{12}$ can contain photoreactive groups such as aryl ketones. Such compounds include 4,5-bis(4-benzoylphenylmethyleneoxy)benzene-1,3-disulfonic acid or its salt; 2,5-bis(4-benzoylphenylmethyleneoxy)benzene-1,4-disulfonic acid or its salt; 2,5-bis(4-benzoylmethyleneoxy)benzene-1-sulfonic acid or its salt; N,N-bis[2-(4-benzoylbenzyloxy)ethyl]-2-aminoethanesulfonic acid or its salt, and the like. See U.S. Pat. No. 6,278,018. The counter ion of the salt can be, for example, ammonium or an alkali metal such as sodium, potassium, or lithium.

In formula V, Q may alternatively be a radical that contains a basic group or a salt thereof. Such Q radicals can include, for example, an ammonium, a phosphonium, or a sulfonium group. The group can be neutral or positively charged, depending upon the pH of the coating composition. In some embodiments, the radical Q includes an ammonium group. Suitable counter ions include, for example, carboxylates, halides, sulfate, and phosphate.

For example, compounds of formula V can have a Q radical that contains an ammonium group; $R^{11}$ and $R^{12}$ can contain photoreactive groups that include aryl ketones. Such photoactivatable cross-linking agents include ethylenebis(4-benzoylbenzyldi-methylammonium) salt; hexamethylenebis(4-benzoylbenzyldimethylammonium) salt; 1,4-bis(4-benzoylbenzyl)-1,4-dimethylpiperazinediium) salt, bis(4-benzoylbenzyl)hexa-methylenetetraminediium salt, bis[2-(4-benzoylbenzyldimethylammonio)ethyl]-4-benzoylhenzylmethylammothum salt; 4,4-bis(4-benzoylbenzyl)morpholinium salt; ethylenehis[(2-(4-benzoylbenzyldimethylammonio)ethyl)-4- benzoylbenzylmethyl-ammonium] salt; and 1,1,4,4-tetrakis (4-benzoylbenzyl)piperzinediium salt. See U.S. Pat. No. 5,714,360. The counter ion is typically a carboxylate ion or a halide. In one embodiment, the halide is bromide.

In other aspects, a non-ionic photoactivatable cross-linking agent can be used. In one embodiment, the non-ionic photoactivatable cross-linking agent has the formula VI: $ZR^{13}R^{14}R^{15}R^{16}$, where Z is a chemical backbone, and $R^{13}$, $R^{14}$, $R^{15}$, and $R^{16}$ are radicals that include a latent photoreactive group. Exemplary non-ionic cross-linking agents of formula VI are those formed by a mixture of the chemical backbone molecule (such as pentaerythritol) and an excess of a derivative of the photoreactive group (such as 4-bromomethylbenzophenone). An exemplary product is tetrakis (4-benzoylbenzyl ether) of pentaerythritol (tetrakis(4-benzoylphenylmethoxy-methypmethane). See U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

Other crosslinking agents which can be used to crosslink the photochrome-containing polymer are described in U.S. Provisional Patent Application Nos. 61/285,435; 61/358,464 and 61/319,127.

If included in a composition, the crosslinking agent can be present at a concentration that can improve the properties of the polymeric matrix (e.g., coating) formed using the photochrome- or near IR dye-containing polymer. A photocrosslinking agent can be used at a concentration in the composition to affect bonding of polymeric material within the composition, or to a device surface, or both, as desired.

The amount of crosslinking agent can be described in terms of the weight by volume in the composition, or the weight of the crosslinker per weight of total polymeric material. In some modes of practice, the composition includes a crosslinking agent in an amount in the range of about 0.2 mg/mL to about 5 mg/mL.

Optionally, a bioactive agent can be included in the polymeric matrix made from a composition including the photochrome- or near IR dye-containing polymer. For example, bioactive agent and the photochrome- or near IR dye-containing polymer can be used to form a bioactive agent-releasing coating on the surface of an insertable or implantable medical device. The coating can enhance use of the device, prevent infection, or treat a pre-existing condition at the location of insertion or implantation. The bioactive agent can be releasable from the polymeric matrix, or can be immobilized on or within the matrix to provide a therapeutic effect.

Exemplary bioactive agents include, but are not limited to, antibiotics, anti-microbials, anti-inflammatory agents, anti-proliferative agents, immunomodulatory agents, anti-mitotics, and anesthetics. Particularly useful bioactive agents of these classes include macrolide antibiotics such as rapamycin (triene macrolide antibiotic) and rapamycin analogs; immunomodulatory agents such as ABT-578; anti-mitotics including taxoid drugs such as paclitaxel and docetaxel; anti-inflammatory agents such as dexamethasone and betamethasone; and anesthetics such as lidocaine or tetracaine.

In some aspects the photochrome- or near IR dye-containing polymer composition is used to coat the surface of a medical device. In particular, the coatings are particularly useful for medical articles that can be inserted into and moved within the body. The coated medical article or device can be any that is introduced temporarily or permanently into a mammal for the prophylaxis or treatment of a medical condition. These articles or devices include any that are introduced subcutaneously, percutaneously or surgically to rest or move within an organ, tissue, or lumen of an organ. In some aspects, the coated medical article is inserted into a portion or portions of the urogenital system, such as the urethra. In some aspects the coated medical article is inserted into a portion or portions of the cardiovascular system, such as an artery, vein, ventricle, or atria of the heart.

The materials that form the structure of the medical device on which the photochrome- or near IR dye-containing polymer can be coated are referred to herein as "article materials" or "device materials" whereas the materials used to form the polymeric coatings are herein referred to as "coating materials." In many cases, the medical article is formed from one or more biomaterial(s) as the coated article is typically placed in contact with biological fluids or tissues following implantation in the body.

A coating including the photochrome- or near IR dye-containing polymer can be formed on any biomaterial surface. Commonly used biomaterial surfaces include plastic materials and metals. Exemplary plastic materials used as device materials include polyvinylchloride (PVC), polytetrafluoroethylene (PTFE), polyethersulfone (PES), polysulfone (PS), polypropylene polyethylene, (PE), polyurethane (PU), polyetherimide (PEI), polycarbonate (PC), and polyetheretherketone (PEEK).

Metals commonly used as device materials include platinum, gold, or tungsten, as well as other metals such as rhenium, palladium, rhodium, ruthenium, titanium, nickel, and alloys of these metals, such as stainless steel, titanium/nickel, nitinol alloys, and platinum/iridium alloys. These metals, including other alloys or combinations, can serve as suitable substrates for disposing the coating composition.

Although many devices or articles are constructed from substantially all metal materials, such as alloys, some may be constructed from both non-metal and metal materials, where at least a portion of the surface of the device is metal. The metal surface may be a thin surface layer. Such surfaces can be formed by any method including sputter coating metal onto all or portions of the surface of the device.

Prior to disposing the coating composition on the surface of the article, the article can be cleaned using any suitable technique.

In some aspects a photochrome- or near IR dye-containing polymeric coating is formed on the surface of a catheter. Exemplary catheters that can be coated included, but are not limited to, guide catheters, urethral catheters, renal catheters, intravenous catheters, artificial lung catheters, blood pressure and stout graft catheters, atherectomy catheters, clot extraction catheters, percutaneous transluminal coronary angioplasty (PTCA) catheters, drug infusion catheters, angiographic catheters, neurological catheters such as neurovascular balloon catheters, thoracic cavity suction drainage catheters, electrophysiology catheters, stroke therapy catheters, abscess drainage catheters, central venous access catheters, hemodialysis catheters, and parental feeding catheters.

To exemplify the benefits that the coatings of the present invention provide to medical devices, a photochrome- or near IR dye-containing polymer coating on the surfaces of a cardiac catheter is discussed.

A cardiovascular catheter is typically a long cylindrically-shaped device made of a plastic material that is inserted into the vasculature of a patent, with the distal end of the catheter advanced through the vasculature to a target location. For example, a catheter is inserted into femoral artery in the groin or the radial artery in the wrist, and advanced into the chambers of the heart or into the coronary arteries. Typically, a guidewire is used to push the catheter to a target location in the body.

A photochrome- or near IR dye-containing polymer-coated catheter can be used for cardiac catheterization. Cardiac catheterization includes procedures such as coronary angiography, as well as left ventrical angiography. Once the catheter is in place, it can be used to perform any one of a number of procedures including angioplasty, angiography, and balloon septostomy.

A photochrome- or near IR dye-containing polymer coated catheter can be used in various analytic procedures, such as measuring blood pressure within the heart, blood oxygenation, and the contractile patterns and strength of cardiac muscle. A photochrome- or near IR dye-containing polymer-coated catheter can also be used in procedures to inject dye into the coronary arteries, such as coronary angiography or coronary arteriography. In this process, a catheter having the photochrome- or near IR dye-containing polymer coating is inserted using a guidewire and advanced towards the heart to a position above the aortic valve. The guidewire is then removed. The catheter is then engaged with the origin of the coronary artery (either left main stem or right coronary artery) and x-ray opaque iodine-based contrast is injected to make the coronary vessels show up on the x-ray fluoroscopy image.

A photochrome- or near IR dye-containing polymer-coated catheter can also be used in balloon-based procedures such as coronary angioplasty (e.g., percutaneous coronary intervention [PCI]).

As another example, a photochrome- or near IR dye-containing polymer coating can be formed on the surface of an endoscopic sheath. Endoscopic sheaths can be used in various medical procedures, including those involving the urogenital tract, the gastrointestinal tract, and the vasculature. For example an endoscope can be delivered through an endoscopic sheath. A photochrome- or near IR dye-containing polymer coating that is lubricious can facilitate movement of the sheath in the body as well as the device within the sheath.

In some aspects a photochrome- or near IR dye-containing polymeric coating is formed on the surface of a prosthetic device. Exemplary prosthetic devices include stents and grafts, such as small diameter grafts, vascular grafts, vascular stents (e.g., self-expanding stents), abdominal aortic aneurysm grafts, urological stents, and esophageal stents.

Other devices that can have a photochrome- or near IR dye-containing polymeric coating include, but are not limited to, introducers (e.g., for guide catheters), electrostimulation (e.g., defibrillator or pacer) leads, defibrillators, biosensors, coronary guidewires, peripheral guidewires, vascular and non-vascular stylets, shunts (e.g., hydrocephalus, and cerebro-spinal fluid shunts), implanted drug infusion tubes, urological implants, urinary dilators, aneurysm exclusion devices, birth control devices, endoscopic devices, blood oxygenator tubing, biliary drainage products, catheter cuffs, tympanostomy vent tubes, and drainage tubes.

In some aspects a photochrome- or near IR dye-containing polymer composition is used to coat the surface of a medical device to provide a lubricious coating. In particular, a lubricious coating is particularly useful for medical articles that can be inserted into and moved within the body, such as the catheters and endoscopic sheaths as described herein.

A photochrome- or near IR dye-containing polymer coating can provide the surface of the medical device with lubricity. As used herein, the term "lubricity" refers to a characterization of the frictional force associated with a coating. A coating with improved lubricity has a lower frictional force. Also, in many aspects, the coating has improved durability.

As used herein, the term "durability" refers to the wear resistance of a polymer coating, or the ability of a coating to adhere to a device surface when subjected to forces typically encountered during use, for example, normal force, shear force, and the like. A more durable coating is less easily removed from a substrate by abrasion. Durability of a coating can be assessed by subjecting the device to conditions that simulate use conditions. Increased durability can be seen when the coated device is subjected to mechanical or physical challenge, such as manipulation of the coated device by bending, twisting, or turning, and/or when the device is in contact with a portion of the body or a portion of another medical article.

As used herein, the term "layer" or "coated layer" will refer to a layer of one or more coated materials of sufficient dimensions (for example, thickness and area) for its intended use over the entire, or less than the entire, portion of an article surface. Therefore, a "coating" as described herein can include one or more "coated layers," each coated layer including one or more coating components. In the least, a coating includes the photochrome-containing polymer of the invention. If the coating includes two or more layers, materials from one coated layer may migrate into an adjacent coated layer(s), depending on the components of a particular coating composition, including the solvent or solution, and dissolved or suspended coating compounds. Therefore, to a certain extent, a coated layer may contain components from an adjacent coated layer, if such a coating arrangement is formed.

One or more additional optional coated layers can be included in the coating. Generally, the photochrome- or near IR dye-containing polymer is located in the coating so that it contacts a body fluid or tissue, and therefore it is generally located at the outermost (e.g. top) portion of the coating. If one or more additional optional coated layers are present in the coating, the additional layer(s) are typically located between the photochrome- or near IR dye-containing polymer and the surface of the device. Therefore, when referring to the step of disposing a photochrome- or near IR dye-containing polymer coating composition on a surface, the surface may be that of the device itself, or the surface of the device with one or more optional coated layers. For purposes of discussion, if an optional layer(s) is present, it can be referred to as an intermediate layer, base layer, or tie layer. The optional layer can also be described relative to the material of the device surface (e.g., "closer/proximal to the surface," "further/distal from the surface," "in contact with the surface," etc.).

An optional coated layer can facilitate formation of the photochrome- or near IR dye-containing polymer on the article. For example, the photochrome- or near IR dye-containing polymer can be disposed on a medical device pre-coated with a non-polymeric silane compound. Exemplary, silane precoatings are described in U.S. Pat. No. 6,706,408.

These types of optional base coated layers can be particularly useful for providing a surface that can be reacted with a latent reactive group, such as a photoreactive group, that can be included in a coating composition or present in the photochrome-containing polymer.

A step in the coating process involves disposing a coating composition including the photochrome- or near IR dye-containing polymer on a surface of a medical article or device. The coating composition can optionally include one or more other polymers, crosslinking compound, and/or other material. If the photochrome- or near IR dye-containing polymer or the composition includes a reactive group, the reactive group can be activated to promote matrix formation, such as by bonding of the photochrome- or near IR dye-containing polymer to a device material or other coating material, or by polymer-polymer crosslinking.

The coating process can be carried out at a temperature suitable to provide a desired coating to the surface, or a portion of the surface, of the article. Preferably, the coating process is carried out at a temperature in the range of 10° C. to 50° C., and more preferably at a temperature in the range of 15° C. to 25° C. However, the actual coating temperature can be chosen based on aspects of the coating composition, including the liquid used to dissolve or suspend the polymeric material, the properties of the polymeric material, and also the method used to dispose the coating composition on the surface of the article.

The coating composition can be applied to the surface of a medical article using any suitable technique. For example, the coating composition can be dipped, sprayed, sponged, or brushed on a device to form a layer, and then dried. In some preferred modes of practice, the coating composition is applied by dip-coating. Optionally, the process can be repeated to provide a coating having multiple coated layers (e.g., multiple layers formed from the photochrome-containing polymer composition). The suitability of the coating composition for use with a particular medical article, and in turn, the suitability of the application technique, can be evaluated by those skilled in the art, given the present description.

A typical dip-coating procedure involves immersing the article to be coated in the coating composition, dwelling the object in the composition for a period of time (a standard time is generally less than about 30 seconds, and can even be less that 10 seconds in many cases), and then removing the article from the composition. After the article has been dip-coated in the coating solution, it is removed and dried. Drying can be carried out using any suitable method, including air-drying the dip coated article. Times up to 30 minutes can be sufficient to dry the coated article although shorter times may be also sufficient.

If the photochrome- or near IR dye-containing polymer or the composition includes a latent photoreactive group, step of irradiating can be performed to activate the latent photoreactive groups in the applied coating materials. For example, the coating can be treated with UV irradiation following the step of disposing the coating composition that includes the photochrome- or near IR dye-containing polymer. The step of activating can be performed before and/or after the coated material dries on the surface of the device. Generally, the step of irradiating can be performed by subjecting the photoreactive groups to actinic radiation in an amount that promotes activation of the photoreactive group and bonding to a target moiety.

Actinic radiation can be provided by any suitable light source that promotes activation of the photoreactive groups. Preferred light sources (such as those available from Dymax Corp.) provide UV irradiation in the range of about 190 nm to about 360 nm, and preferably from about 190 nm to about 290 nm. A suitable dose of radiation is in the range of about 0.5 mW/cm$^2$ to about 2.0 mW/cm$^2$.

In some methods, filters are used in connection with the step of activating the photoreactive groups. The use of filters can be beneficial from the standpoint that they selectively minimize the amount of radiation of a particular wavelength or wavelengths that can be subsequently used to cause ring opening of the photochrome moiety. In this sense, during the irradiation of the photoreactive groups causing covalent bonding, the photochrome moiety does not become "bleached out" and lose its ability to provide a coloring effect after the coating has been formed.

Typically, filters are identified by the wavelength of light that is permitted to pass through the filter. Two illustrative types of filters that can be used in connection with the invention are cut-off filters and band pass filters. Generally, cut-off filters are categorized by a cut-off transmittance, where the light transmittance is approximately 25% of the maximum transmittance. For band pass filters, a range of wavelength is identified for the filter, and the center wavelength is the midpoint of wavelength allowed through; at midpoint, the transmittance is approximately half of the maximum transmittance allowed through the filter. Thus, in one embodiment utilizing a band pass filter, for example, an Edmund 407 rim filter, the filter can be chosen that has a maximum UV transmittance at its center wavelength of 407 nm. In another embodiment, a band pass filter having a maximum transmittance at 500 rim is used. A polymer composition including the photochrome- or near IR dye-containing polymer can also include a small molecule stabilizer, such as a tertiary amines and inorganic salts, such as zinc, nickel, copper salts. These types of stabilizers can hydrogen bond or coordinate with the photochrome or dye and prevent free radical attack, thereby reducing a bleaching effect on the photochrome or dye. Once the polymeric matrix is formed, such as a coating, the stabilizer can be rinsed out of the matrix if desired.

Filters may optionally be used for preparing matrices from polymers having a pendent near IR dye and latent UV photoreactive group, but generally are not required because of the significant gap between the activation wavelengths of the UV activated photogroup and the near IR dye. Preferred UV light sources generally cause little or no bleaching of near IR dyes, and therefore polymers having these two particular types of pendent groups are attractive for forming durable detectable lubricious coatings. The coating process can be carried out to provide a coating having a desired thickness that is suitable for the device that is being coated and the method that the coated device is being used for. The coating including the photochrome- or near IR dye-containing polymer can also be described in terms of thickness. It is understood that a very thin coated layer (e.g., such as about 0.5 µm dried) can be formed on the surface device, as well as substantially thick coatings (e.g., such as about 5 mm dried). Thicker coatings can be formed by sequentially applying a coating composition including the photochrome- or near IR dye-containing polymer. The coating thickness can also be controlled by varying the liquid in the composition, as well as by changing the concentration of the photochrome- or near IR dye-containing polymer in solution. For use on an implantable medical device, such as a catheter, the coating thickness can fall within a preferred range of thickness.

After the photochrome- or near IR dye-containing polymer is applied on a surface or formed into a desired article, it can be irradiated to provide visualization or detection of the material. With regards to the photochrome, any light source that provides light radiation of a wavelength capable of causing opening of the ring structure in the photochrome moiety can be used (herein referred to as the "photochrome excitation wavelength"). In some preferred modes of practice, a light source that provides narrow band wavelength emission is used to cause photochrome visualization. This can be useful if material in the polymeric article is sensitive to wavelengths outside of the photochrome excitation wavelength.

Typical photochrome excitation wavelengths are in the range of about 290 nm to about 450 nm or greater, and more typically between about 310 nm to about 400 nm. Exemplary light sources capable of providing irradiation in this wavelength include conventional halogen lamps, fast halogen lamps, argon-ion lasers, plasma arc, LED (light emitting diode)-based sources. Light sources capable of providing light radiation in this wavelength are commercially available from, for example Dymax (Torrington, Conn.), or EFOS, Inc. (Mississauga, Ontario, Canada).

With regards to the near IR dye, any light source that provides light radiation of a wavelength capable of causing near IR emission from the dye can be used (herein referred to as the "near IR dye excitation wavelength"). Typical near IR excitation wavelengths are in the range of about 650 rim to about 800 rim or greater. Exemplary light sources capable of providing irradiation in this wavelength include far red LED emitters, far red lasers, low-power near-infrared continuous-wave laser diodes, and infrared lasers, including titanium-doped sapphire (Ti:sapphire). Light sources capable of providing light radiation in this wavelength are commercially available from, for example Quantum Devices, Inc. (Bameveld, Wis.).

An amount of light irradiation can be applied to the photochrome- or near IR dye-containing polymer sufficient to promote transformation of the photochrome or near IR dye and desired visualization of the polymeric material. The amount of light irradiation provided to the polymeric material will depend on the intensity of the light source, the distance of the light source to the polymeric material, and the amount of time the light is applied to the polymeric material.

Generally, higher loading of the photochrome or near IR dye on the polymer will provide a more intense color or more intense IR radiation upon irradiation and ring opening. A more intense color or emitted IR radiation can also be seen according to the amount of polymeric material. For example, in the case of coatings, a more intense color or IR radiation can also be seen if one area of the coating is thicker than another area of coating.

The use of the photochrome or near IR dye enables visual assessment of coating quality, including thickness. The presence of the photochrome or near IR dye can also be useful for determining if the coating includes any undesirable features or irregularities. For example, visualization via the photochrome or near IR dye can allow the determination of any coating cracks or areas of delamination.

Use of a photochrome or near IR dye can also facilitate the application of a polymeric material to a desired area of the body. Tissue treatment methods can involve the application of a photochrome- or near IR dye-containing polymer to a target location in an in situ process. At the target site the polymeric material can be treated to cause crosslinking of the polymer and formation of a polymeric matrix. The target area can be irradiated, and the presence and/or attributes of the formed polymeric matrix can be assessed. Without the presence of the photochrome or near IR dye it may be difficult to assess whether the polymeric matrix was formed on the desired tissue site and/or with the desired attributes, such as thickness, etc. If desired, the photochrome- or near IR dye-containing polymer can be reapplied to the target site to cover area that was missed in the first application, or to build up the thickness of the applied material.

The use of a near IR dye is particularly advantageous for applications involving forming and detecting a polymeric matrix at a target site in the body, such as one where the matrix is in contact with tissue. Because cell and tissue components produce minimal autofluorescence in the near-IR region, a polymer with pendent near-IR dye moieties can provide a highly specific and sensitive method for detecting the matrix.

Visualization of the polymeric material can be enhanced by reducing or eliminating the amount of background light.

After the photochrome- or near IR dye-containing polymer coating has been formed on the surface of a device (such as a catheter, for example) the coated device can optionally be sterilized prior to use. While any type of sterilization procedure can be employed, one preferred procedure involves treatment with ethylene oxide.

Sterilization with ethylene oxide offers the advantage of avoiding the higher temperatures or the moisture associated with steam sterilization. Another advantage of ethylene oxide is that its residues volatilize relatively quickly from the article sterilized. Since ethylene oxide is a highly flammable material it is generally used in a mixture with a flame retardant. Commonly used flame retardant compounds include chlorofluorocarbons (CFCs) such as dichlorodifluoro-methane (also known as CFC 12), and carbon dioxide. Other components that can be present in mixture with ethylene oxide include inert nitrogen gas, which may be used to increase the pressure in the sterilization chamber.

An exemplary ethylene oxide sterilization is carried out as follows. The coated device is placed in a commercially available sterilization chamber. The chamber is then heated to a temperature within the range of from about 54° C. (130° F.) to about 60° C. (140° F.). A partial vacuum is created in the chamber with the addition of water vapor to provide a relative humidity in the range of about 30 to about 80 percent. The sterilant mixture is then converted to a vapor and introduced into the sterilization chamber at a pressure in the range of about 362.0 millimeter of mercury (0° C.; 7 psi) to about 1706.6 millimeter of mercury (0° C.; 33 psi). The sterilization time can vary and is dependent upon a number of factors including temperature, pressure, humidity level, the specific sterilant mixture employed, and the coated device. Following exposure the ethylene oxide is evacuated from the chamber, for example, by flushing with air, nitrogen, steam or carbon dioxide.

EXAMPLE 1

A spiropyran-based monomer is prepared by the reaction of 2,3,3-trimethyl-3H-indole (compound A) with bromomethyl benzoic acid (compound B) in the presence of acetonitrile (ACN) to provide compound (C).

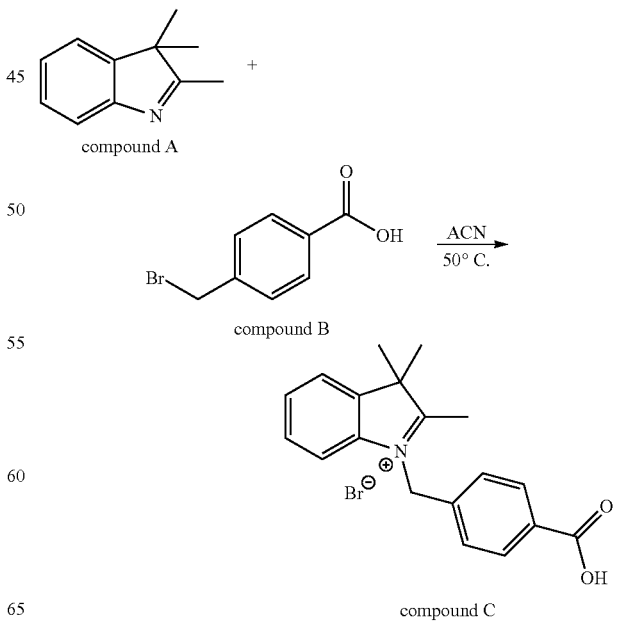

Compound C is reacted with 2-hydroxy-5-nitro-benzaldehyde (compound D) in the presence of triethylamine (NEt₃) to complete the photochrome moiety to provide compound (E).

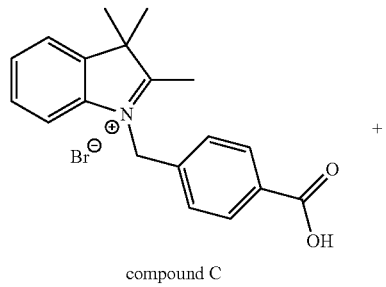
compound C

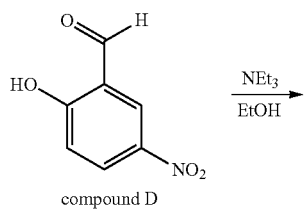
compound D

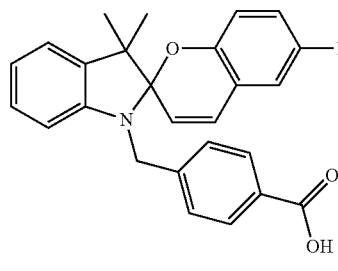
compound E

Intermediate compound E is reacted with ethyleneglycol monoacrylate (compound F) in the presence of DIC (diisopropylcarbodiimide) and DMAP (4-(dimethylamino)pyridine)) under basic conditions to provide the final compound (G) which is a photochrome-coupled monomer.

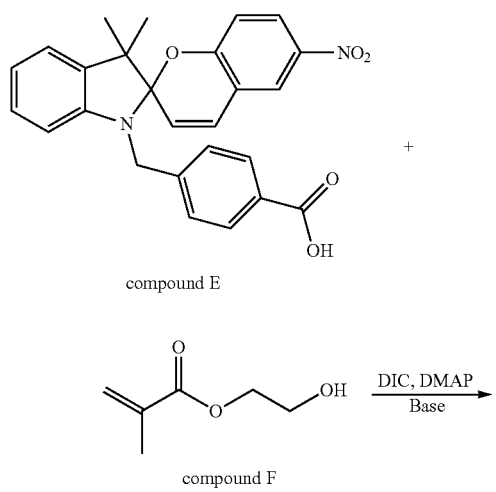
compound E compound F

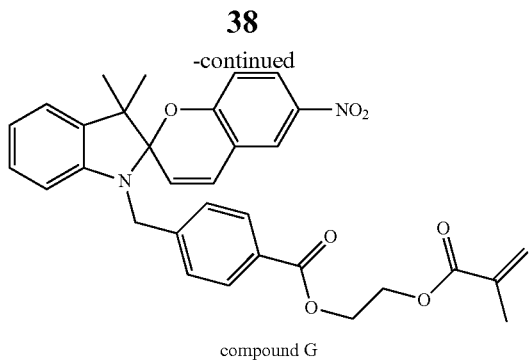
compound G

What is claimed is:

1. A medical article having a lubricious coating, the coating comprising a biocompatible hydrophilic copolymer having a polymeric backbone, the copolymer comprising
   a hydrophilic monomer, and
   a monomer comprising a detectable moiety according to the following formula:

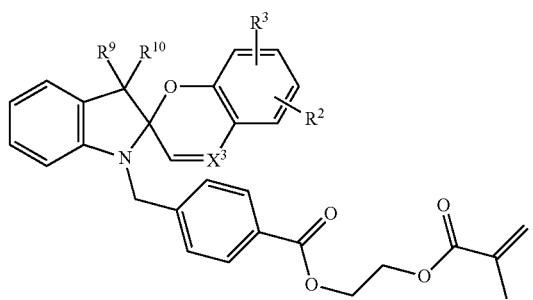

wherein $R^9$ and $R^{10}$ are independently selected from —H and —CH₃, $X^3$ is N or C, and $R^2$ and/or $R^3$ are independently selected from electron withdrawing groups selected from the group consisting of nitro (—NO₂), quaternary amine, trihalide, cyano, sulfonate, carboxylic acid, and ester, wherein if $R^2$ or $R^3$ is not an electron withdrawing group, then it is H.

2. The medical article of claim 1 wherein $X^3$ is C; or $R^2$ is nitro (—NO₂) and $R^3$ is H; or $X^3$ is C, $R^2$ is nitro (—NO₂) and $R^3$ is H.

3. The medical article of claim 2, wherein the monomer comprising a detectable moiety pendent according to the following formula:

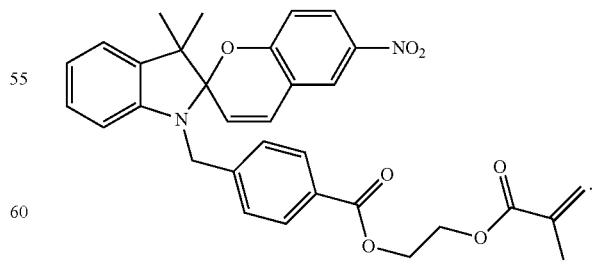

4. The medical article of claim 1, wherein the copolymer further comprises a monomer comprising a pendant reactive group that allows for polymer crosslinking or bonding of the polymer to a target upon activation of the reactive group.

5. The medical article of claim 1, wherein the monomer comprising the detectable moiety is present in the polymer in an amount in the range of 0.1% mol to 25% mol (monomer/polymer).

6. The medical article of claim 4 wherein the pendent reactive group comprises an aryl ketone photoreactive group.

7. The medical article of claim 1 comprising a catheter, wherein the lubricious coating is formed on a surface of the catheter.

8. The medical article of claim 1 wherein the medical article comprises a bioactive agent.

9. The medical article of claim 1 wherein the hydrophilic monomer is selected from the group consisting of methacrylate, methyl methacrylate, hydroxyethyl methacrylate, hydroxyethyl acrylate, glycerol acrylate, glycerol methacrylate, acrylamide, methacrylamide, aminopropylmethacrylamide, methyl vinyl ether, vinyl pyrrolidone, and mixtures thereof.

* * * * *